United States Patent
Zavanelli et al.

(10) Patent No.: US 12,171,576 B1
(45) Date of Patent: Dec. 24, 2024

(54) PATCH FOR IMPROVED BIOMETRIC DATA CAPTURE AND RELATED PROCESSES

(71) Applicant: Huxley Medical, Inc., Atlanta, GA (US)

(72) Inventors: Nathan Zavanelli, Atlanta, GA (US); Brennan Torstrick, Atlanta, GA (US); Nick Bolus, Birmingham, AL (US); Mohsen Safaei, Smyrna, GA (US); Brett Klosterhoff, St. Louis, MO (US)

(73) Assignee: Huxley Medical, Inc., Atlanta, GA (US)

( * ) Notice: Subject to any disclaimer, the term of this patent is extended or adjusted under 35 U.S.C. 154(b) by 0 days.

(21) Appl. No.: 18/339,187

(22) Filed: Jun. 21, 2023

Related U.S. Application Data

(60) Continuation of application No. 17/929,475, filed on Sep. 2, 2022, now Pat. No. 11,717,221, which is a division of application No. 17/199,181, filed on Mar. 11, 2021, now Pat. No. 11,464,451.
(Continued)

(51) Int. Cl.
  *A61B 5/0295* (2006.01)
  *A61B 5/00* (2006.01)
  *A61B 5/0205* (2006.01)

(52) U.S. Cl.
  CPC .......... *A61B 5/6833* (2013.01); *A61B 5/0205* (2013.01); *A61B 5/725* (2013.01); *A61B 2560/0214* (2013.01); *A61B 2562/0219* (2013.01); *A61B 2562/043* (2013.01); *A61B 2562/166* (2013.01)

(58) Field of Classification Search
  CPC ..................... A61B 5/02416; A61B 2562/0219
  See application file for complete search history.

(56) References Cited

U.S. PATENT DOCUMENTS

| | | | |
|---|---|---|---|
| 1,248,586 | A | 12/1917 | Wood |
| 3,052,232 | A | 9/1962 | Zworykin |

(Continued)

FOREIGN PATENT DOCUMENTS

| | | |
|---|---|---|
| AU | 2015253309 | 11/2015 |
| CN | 218978894 U | 5/2023 |

(Continued)

OTHER PUBLICATIONS

Barker, Signal Extraction Technology, Nov. 30, 2009, 45 pages.
(Continued)

*Primary Examiner* — Michael J D'Abreu
(74) *Attorney, Agent, or Firm* — Husch Blackwell LLP; Bryan D. Stewart

(57) ABSTRACT

A conformal patch device can be provided to a patient. The patch device can include sensors configured to be positioned over a chest of a patient. The sensors can include PPG sensors, ECG sensors, and SCG sensors. The conformal patch device can adhere to a single continuous area of the chest. Some sensors may attached to a viscoelastic substrate to achieve mechanical isolation from other patch components. The conformal patch device can capture measurements from the sensor doing a time window sufficient enough to detect disordered breathing. The system can determine disordered breathing and related cardiorespiratory parameters during the time window for the patient using the sensor measurements.

20 Claims, 21 Drawing Sheets

Related U.S. Application Data

(60) Provisional application No. 63/024,930, filed on May 14, 2020, provisional application No. 62/988,087, filed on Mar. 11, 2020.

(56) References Cited

U.S. PATENT DOCUMENTS

| | | | |
|---|---|---|---|
| 3,195,535 | A | 7/1965 | Westermann |
| 3,638,642 | A | 2/1972 | Heflin |
| 4,104,728 | A | 8/1978 | Kasubuchi |
| 4,121,573 | A | 10/1978 | Crovella |
| 4,957,109 | A | 9/1990 | Groeger |
| 5,050,613 | A * | 9/1991 | Newman ............ A61B 5/7435 600/490 |
| 5,251,286 | A | 10/1993 | Weiner |
| 5,307,818 | A | 5/1994 | Segalowitz |
| 5,546,811 | A | 8/1996 | Rogers |
| 5,633,711 | A | 5/1997 | Nelson |
| 5,672,830 | A | 9/1997 | Rogers |
| 5,734,470 | A | 3/1998 | Rogers |
| 5,800,478 | A | 9/1998 | Chen |
| 5,812,261 | A | 9/1998 | Nelson |
| 5,951,881 | A | 9/1999 | Rogers |
| 5,982,482 | A | 11/1999 | Nelson |
| 6,016,202 | A | 1/2000 | Fuchs |
| 6,033,202 | A | 3/2000 | Bao |
| 6,052,185 | A | 4/2000 | Banet |
| 6,069,703 | A | 5/2000 | Banet |
| 6,148,127 | A | 11/2000 | Adams |
| 6,150,668 | A | 11/2000 | Bao |
| 6,169,831 | B1 | 1/2001 | Adams |
| 6,181,852 | B1 | 1/2001 | Adams |
| 6,192,177 | B1 | 2/2001 | Admunson |
| 6,252,253 | B1 | 6/2001 | Bao |
| 6,256,100 | B1 | 7/2001 | Banet |
| 6,275,629 | B1 | 8/2001 | Eggleton |
| 6,285,812 | B1 | 9/2001 | Admunson |
| 6,303,182 | B1 | 10/2001 | Eggleton |
| 6,307,988 | B1 | 10/2001 | Eggleton |
| 6,329,226 | B1 | 12/2001 | Jones |
| 6,337,761 | B1 | 1/2002 | Rogers |
| 6,351,585 | B1 | 2/2002 | Amundson |
| 6,363,096 | B1 | 3/2002 | Dodabalapur |
| 6,370,300 | B1 | 4/2002 | Eggleton |
| 6,410,416 | B1 | 6/2002 | Dodabalapur |
| 6,427,040 | B1 | 7/2002 | Ahuja |
| 6,438,277 | B1 | 8/2002 | Eggleton |
| 6,529,676 | B2 | 3/2003 | Eggleton |
| 6,589,629 | B1 | 7/2003 | Bao |
| 6,655,286 | B2 | 12/2003 | Rogers |
| 6,719,868 | B1 | 4/2004 | Schueller |
| 6,736,985 | B1 | 5/2004 | Bao |
| 6,743,982 | B2 | 6/2004 | Biegesen |
| 6,753,131 | B1 | 6/2004 | Rogers |
| 6,769,769 | B2 | 8/2004 | Podoleanu |
| 6,778,734 | B2 | 8/2004 | Baldwin |
| 6,795,198 | B1 | 9/2004 | Fuchs |
| 6,829,415 | B2 | 12/2004 | Kroupenkine |
| 6,856,731 | B2 | 2/2005 | Rogers |
| 6,895,688 | B2 | 5/2005 | Acharya |
| 6,927,860 | B2 | 8/2005 | Podoleanu |
| 6,946,332 | B2 | 9/2005 | Loo |
| 7,110,646 | B2 | 9/2006 | Eggleton |
| 7,139,478 | B2 | 11/2006 | Eggleton |
| 7,195,733 | B2 | 3/2007 | Rogers |
| 7,229,847 | B2 | 6/2007 | Hsu |
| 7,330,273 | B2 | 2/2008 | Podoleanu |
| 7,417,741 | B2 | 8/2008 | Podoleanu |
| 7,439,096 | B2 | 10/2008 | Baldwin |
| 7,521,292 | B2 | 4/2009 | Rogers |
| 7,557,367 | B2 | 7/2009 | Rogers |
| 7,704,684 | B2 | 4/2010 | Rogers |
| 7,705,280 | B2 | 4/2010 | Nuzzo |
| 7,799,699 | B2 | 9/2010 | Nuzzo |
| 7,943,491 | B2 | 5/2011 | Nuzzo |
| 8,372,726 | B2 | 2/2013 | De Graff |
| 8,734,339 | B2 | 5/2014 | Rao |
| 9,061,494 | B2 | 6/2015 | Rogers |
| 9,119,533 | B2 | 9/2015 | Ghaffari |
| 9,247,637 | B2 | 1/2016 | Hsu |
| 9,372,123 | B2 | 6/2016 | Li |
| 9,545,285 | B2 | 1/2017 | Ghaffari |
| 9,554,850 | B2 | 1/2017 | Lee |
| 9,579,040 | B2 | 2/2017 | Rafferty |
| 9,613,911 | B2 | 4/2017 | Rogers |
| 9,622,680 | B2 | 4/2017 | Ghaffari |
| 9,629,586 | B2 | 4/2017 | Ghaffari |
| 9,702,839 | B2 | 7/2017 | Ghaffari |
| 9,704,908 | B2 | 7/2017 | De Graff |
| 9,706,647 | B2 | 7/2017 | Hsu |
| 9,723,122 | B2 | 8/2017 | Ghaffari |
| 9,723,711 | B2 | 8/2017 | Elolampi |
| 9,750,421 | B2 | 9/2017 | Ghaffari |
| 9,757,050 | B2 | 9/2017 | Ghaffari |
| 9,810,623 | B2 | 11/2017 | Ghaffari |
| 9,744,145 | B1 | 12/2017 | Hsu |
| 9,746,829 | B2 | 12/2017 | Fastert |
| 9,833,190 | B2 | 12/2017 | Ghaffari |
| 9,894,757 | B2 | 2/2018 | Arora |
| 9,899,330 | B2 | 2/2018 | Dalal |
| 9,949,691 | B2 | 4/2018 | Huppert |
| 10,024,743 | B2 | 7/2018 | Davis |
| 10,032,709 | B2 | 7/2018 | Rafferty |
| D825,537 | S | 8/2018 | Li |
| 10,161,737 | B2 | 12/2018 | Pegan |
| 10,186,546 | B2 | 1/2019 | De Graff |
| 10,192,830 | B2 | 1/2019 | Rogers |
| 10,582,618 | B2 | 3/2020 | Coleman |
| 10,898,084 | B2 | 1/2021 | Khine |
| 11,207,002 | B2 | 12/2021 | Khine |
| 2002/0180605 | A1 | 12/2002 | Ozguz |
| 2005/0096513 | A1 | 5/2005 | Ozguz |
| 2014/0275845 | A1 | 9/2014 | Eagon |
| 2014/0275888 | A1 | 9/2014 | Wegerich |
| 2015/0351689 | A1 | 12/2015 | Adams |
| 2016/0302674 | A1 | 10/2016 | Moyer |
| 2016/0313176 | A1 * | 10/2016 | Lee ............ A61B 5/02438 |
| 2017/0079144 | A1 | 3/2017 | Coleman |
| 2017/0156623 | A1 | 6/2017 | Chu |
| 2017/0347894 | A1 * | 12/2017 | Bhushan ............ A61B 5/14542 |
| 2018/0177459 | A1 * | 6/2018 | Eletr ............ A61B 5/02125 |
| 2019/0069788 | A1 | 3/2019 | Coleman |
| 2019/0113326 | A1 | 4/2019 | Pegan |
| 2019/0142625 | A1 | 5/2019 | Goff |
| 2020/0069193 | A1 | 3/2020 | Khine |
| 2020/0255791 | A1 | 8/2020 | Yeo |
| 2021/0161405 | A1 | 6/2021 | Khine |
| 2022/0009764 | A1 | 1/2022 | Zhou |
| 2022/0280066 | A1 | 9/2022 | Chu |

FOREIGN PATENT DOCUMENTS

| | | |
|---|---|---|
| EP | 3083248 | 8/2017 |
| EP | 3673797 | 7/2020 |
| EP | 3673797 A1 * | 7/2020 |
| EP | 3137038 | 12/2020 |
| EP | 3877830 | 8/2022 |
| WO | 2015095836 | 6/2015 |
| WO | 2015179320 | 11/2015 |
| WO | 2015179322 | 11/2015 |
| WO | 2017220526 | 12/2017 |
| WO | 2020092747 | 5/2020 |
| WO | 2020097505 | 5/2020 |
| WO | 2020228724 | 11/2020 |
| WO | 2021055496 | 3/2021 |
| WO | 2021142121 | 7/2021 |

OTHER PUBLICATIONS

Bicen, et al., A Signal Quality Index for Ballistocardiogram Recordings based on Electrocardiogram RR Intervals and Matched Filtering, IEEE EMBS International Conference on Biomedical & Health Informatics (BHI), Mar. 2018, 4 pages, Las Vegas.

(56) References Cited

OTHER PUBLICATIONS

Biometrics, et al., Medical electrical equipment—Part 2-61: Particular requirements for basic safety and essential performance of pulse oximeter equipment, International Standard, 2018, 100 pages, vol. 2.0, Geneva.
Boe, et al., Automating sleep stage classification using wireless wearable sensors, npj Digital Medicine, 2019, 9 pages.
Brüser, et al., Ambient and Unobtrusive Cardiorespiratory Monitoring Techniques, IEEE Reviews in Biomedical Engineering, 2015, 14 pages, vol. 8.
Bsoul, et al., Real-Time Sleep Quality Assessment Using Single-Lead ECG and Multi-Stage SVM Classifier, IEEE, Sep. 2010, 4 pages, Buenos Aires.
Bsoul, et al., Apnea MedAssist: Real-time Sleep Apnea Monitor Using Single-Lead ECG, IEEE Transactions on Information Technology in Biomedicine, May 2011, 12 pages, vol. 15.
Budidha, et al., Investigation of Pulse Transit Times utilizing multisite reflectance photoplethysmography under conditions of artificially induced peripheral vasoconstriction. 2014 36th Annual International Conference of the IEEE Engineering in Medicine and Biology Society (EMBC), pp. 1965-1968. doi: 10.1109/EMBC.2014.6943998.
Budidha, et al., Investigation of photoplethysmography and arterial blood oxygen saturation from the ear-canal and the finger under conditions of artificially induced hypothermia, IEEE Engineering in Medicine and Biology Society Conference, Aug. 2015, 5 pages.
Budidha, et al., Photoplethysmography for Quantitative Assessment of Sympathetic Nerve Activity (SNA) During Cold Stress, Front, Physiol, 9:1863, 2019, 10 pages, doi: 10.3389/fphys.2018.01863.
Carek, et al., SeismoWatch: Wearable Cuffless Blood Pressure Monitoring Using Pulse Transit Time, Proc. ACM Interact. Mob. Wearable Ubiquitous Technol. 1, 3, Article 40, Sep. 2017, 16 pages.
Castiglioni, et al., Seismocardiography While Sleeping at High Altitude, IEEE EMBS, Aug. 2012, 4 pages.
Choudhary, et al., Automatic Detection of Aortic Valve Opening Using Seismocardiography in Healthy Individuals, IEEE Journal of Biomedical and Health Informatics, May 2019, 9 pages, vol. 23, No. 3.
Chreiteh, Investigation of Sternal Photoplethysmography—Design of a Vital Sign Patch, Technical University of Denmark, Mar. 2016, 187 pages.
Clifford, et al., Signal Processing Methods for Heart Rate Variability, St. Cross College, 2002, 244 pages.
Clifford, et al., Signal quality in cardiorespiratory monitoring, Physiol. Meas. 33 E01, 2012, 6 pages.
Dassel, et al., Effect of location of the sensor on reflectance pulse oximetry, British Journal of Obstetrics and Gynaecology, Aug. 1997, pp. 910-916, vol. 104.
Dehkordi, et al., Comparison of Different Methods for Estimating Cardiac Timings: A Comprehensive Multimodal Echocardiography Investigation, Front. Physiol. 10:1057, Aug. 2019, 11 pages.
Di Rienzo, et al., Wearable seismocardiography: Towards a beat-by-beat assessment of cardiac mechanics in ambulant subjects, Autonomic Neuroscience: Basic and Clinical, Apr. 2013, 10 pages.
Etemadi, et al., Non-Invasive Assessment of Cardiac Contractility on a Weighing Scale, IEEE EMBS, Sep. 2009, 4 pages.
Etemadi, et al., A Wearable Patch to Enable Long-Term Monitoring of Environmental, Activity and Hemodynamics Variables, IEEE Transactions on Biomedical Circuits and Systems, 2016, 9 pages.
Etemadi, et al., Wearable Ballistocardiogram and Seismocardiogram Systems for Health and Performance, Press. J Appl Physiol, Aug. 2017, 35 pages.
Fonseca, et al., Sleep stage classification with ECG and respiratory effort, Physiological Measurement, 2015, 15 pages, vol. 36.
Gao, et al., Obstructive sleep apnea syndrome detection based on ballistocardiogram via machine learning approach, Mathematical Biosceinces and Engineering, Jun. 2019, 15 pages.
Goldman, et al., Masimo Signal Extraction Pulse Oximetry, Journal of Clinical Monitoring and Computing, Jan. 2000, 9 pages, vol. 16, Kluwer Academic Publishers, Netherlands.

Graybeal, et al., Adaptive Filtering and Alternative Calculations Revolutionizes Pulse Oximetry Sensitivity and Specificity During Motion and Low Perfusion, IEEE EMBS, Sep. 2004, 4 pages.
Gupta, et al., Precision wearable accelerometer contact microphones for longitudinal monitoring of mechano-acoustic cardiopulmonary signals, npj Digital medicine, 2020, 8 pages.
Haahr, et al., An Electronic Patch for Wearable Health Monitoring by Reflectance Pulse Oximetry, IEEE Transactions on Biomedical Circuits and Systems, Feb. 2012, 9 pages, vol. 6 No. 1.
Hartmann, et al., Quantitative Comparison of Photoplethysmographic Waveform Characteristics: Effect of Measurement Site, front. Physiol., Mar. 2019, 8 pages.
He, et al., Secondary Peak Detection of PPG Signal for Continuous Cuffless Arterial Blood Pressure Measurement, IEEE Transactions on Instrumentation and Measurement, Jun. 2014, 9 pages.
Hossein, et al., Accurate Detection of Dobutamineinduced Haemodynamic Changes by Kino-Cardiography: A Randomised Double-Blind placebo-Controlled Validation study, Scientific Reports, Jul. 2019, 11 pages.
Hsu, et al., Screening of obstructive sleep apnea in patients who snore using a patch-type device with electrocardiogram and 3-axis accelerometer, Journal of Clinical Sleep Medicine, 2020, 12 pages.
Hung, Central Sleep Apnea Detection Using an Accelerometer, Association for Computing Machinery, Jun. 2018, 6 pages.
Hung, et al., Estimation of Respiratory Waveform Using an Accelerometer, IEEE ISBI, 2008, 4 pages.
Inan, Wearable Sensing of Left Ventricular Function, Spring International Publishing, Mobile Health, 2017, 23 pages.
Inan, et al., Ballistocardiography and Seismocardiography: A Review of Recent Advances, IEEE Journal of Biomedical and Health Informatics, 2014, 30 pages.
Inan, et al., Novel Wearable Seismocardiography and Machine Learning Algorithms Can Assess Clinical Status of Heart Failure Patients, Circ Heart Fail., 2018, 10 pages.
Inan, et al., Evaluating the Lower-Body Electromyogram Signal Acquired From the Feet as a Noise Reference for Standing Ballistocardiogram Measurements, IEEE Transactions on Information Technology in Biomedicine, Sep. 2010, 9 pages, vol. 14 No. 5.
Javaid, et al., Quantification of Posture Induced Changes in Wearable Seismocardiogram Signals for Heart Failure Patients, Computing in Cardiology, 2016, 4 pages, vol. 43.
Jensen, Signal Processing of Nano Sensor Data, Kongens Lyngby, Mar. 2009, 127 pages.
Jensen, et al., Independent Component Analysis Applied to Pulse Oximetry in the Estimation of the Arterial Oxygen Saturation (SpO2)—a Comparative Study, IEEE EMBS, Sep. 2009, 7 pages.
Johnston, Development of a Signal Processing Library for Extraction of SpO2, HR, HRV, and RR from Photoplethysmographic Waveforms, Worcester Polytechnic Institute, 2006, 148 pages.
Khosrow-Khavar, et al., Automatic and Robust Delineation of the Fiducial Points of the Seismocardiogram Signal for Noninvasive Estimation of Cardiac Time Intervals, IEEE Transactions on Biomedical Engineering, Aug. 2017, 10 pages, vol. 64. No. 8.
Kramer, et al., Wearable Pulse Oximetry Measurements on the Torso, Arms, and Legs: A Proof of Concept, Military Medicine, 2017, 7 pages.
Li, et al., Principle Component Analysis on Photoplethysmograms: Blood Oxygen Saturation Estimation and Signal Segmentation, IEEE EMBS, Sep. 2011, 4 pages.
Liang, et al., Analysis: An optimal filter for short photoplethysmogram signals, Scientific Data, May 2018, 12 pages.
Longmore, et al., A Comparison of Reflective Photoplethysmography for Detection of Heart Rate, Blood Oxygen Saturation, and Respiration Rate at Various Anatomical Locations, Sensors, Apr. 2019, 19 pages.
Mendelson, et al., Noninvasive Pulse Oximetry Utilizing Skin Reflectance Photoplethysmography, IEEE Transactions on Biomedical Engineering, Oct. 1988, 8 pages, vol. 35 No. 10.
Morra, et al., Modification of the mechanical cardiac performance during end-expiratory voluntary apnea recorded with ballistocardiography and seismocardiography, Physiological Measurement, 2019, 32 pages.

(56) References Cited

OTHER PUBLICATIONS

Morra, et al., Ballistocardiography and Seismocardiography detect hemodynamic changes during simulated obstructive apnea, Physiological Measurement, 2020, 34 pages.
Munck, et al., Multichannel seismocardiography: an imaging modality for investigating heart vibrations, Physiological Measurement, 2020, 12 pages, vol. 41.
Muthasamy, et al., An Overview of Respiratory Airflow Estimation Techniques: Acoustic vs Non-Acoustic, IEEE International Conference on Signal and Image Processing Applications, Sep. 2019, 5 pages.
Nara, et al., Novel Notch Detection Algorithm for Detection of Dicrotic Notch in PPG Signals, International Journal of Computer Applications, Jan. 2014, 5 pages, vol. 86 No. 17.
Nilsson, et al., Combined photoplethysmographic monitoring of respiration rate and pulse: a comparison between different measurement sites in spontaneously breathing subjects, Acta Anaesthesiol Scand, 2007, 8 pages, vol. 51.
Pandey, et al., Pulse Oximeter for Low SpO2 Level Detection Using Discrete Time Signal Processing Algorithm, Journal of Medical Devices, Jun. 2019, 8 pages, vol. 18.
Pandia, et al., Motion Artifact Cancellation to Obtain Heart Sounds From a Single Chest-Worn Accelerometer, IEEE ICASSP, 2010, 4 pages.
Pandia, et al., Extracting respiratory information from seismocardiogram signals acquired on the chest using a miniature accelerometer, Physiological Measurement, Sep. 2012, 19 pages, vol. 33.
Pandia, et al., A Frequency Domain Analysis of Respiratory Variations in the Seismocardiogram Signal, IEEE EMBS, Jul. 2013, 4 pages.
Racape, et al., Influence of sympathetic activation on myocardial contractility measured with ballistocardiography and seismocardiography during sustained end-expiratory apnea, Am J Physiol Regul Integr Comp Physiol, Sep. 2020, 10 pages.
Razjouyan, et al., Improving Sleep Quality Assessment Using Wearable Sensors by Including Information From Postural/Sleep Position Changes and Body Acceleration: A Comparison of Chest-Worn Sensors, Wrist Actigraphy, and Polysomnography, Journal of Clinical Sleep Medicine, 2017, 10 pages, vol. 13 No. 11.
Rusch, et al., Alternate Pulse Oximetry Algorithms for Sp02 Computation, University of South Florida, 1994, 2 pages.
Rusch, et al., Signal Processing Methods for Pulse Oximetry, Comput. Biol. Med., Oct. 1995, 17 pages, vol. 26 No. 2.
Morillo, et al., An Accelerometer-Based Device for Sleep Apnea Screening, IEEE Transactions on Information Technology in Biomedicine, Mar. 2010, 9 pages, vol. 10 No. 2.
Schlotthauer, et al., Measuring Complexity of Biomedical Signals, Hindawi Complexity, 2018, 4 pages, vol. 2018.
Shafiq, et al., Data Descriptor: Multimodal chest surface motion data for respiratory and cardiovascular monitoring applications, Scientific Data, Apr. 2017, 12 pages.
Skoric, et al., Relationship of the Respiration Waveform to a Chest Worn Inertial Sensor, IEEE, 2020, 4 pages.
Solà, et al., Chest Pulse-Wave Velocity: A Novel Approach to Assess Arterial Stiffness, IEEE Transactions on Biomedical Engineering, Jan. 2011, 9 pages, vol. 58 No. 1.
Sørensen, et al., Definition of Fiducial Points in the Normal Seismocardiogram, Scientific Reports, Oct. 2018, 11 pages.
Taebi, et al., Recent Advances in Seismocardiography, Vibration, 2019, 23 pages, vol. 2.
Tamura, Current progress of photoplethysmography and SPO2 for health monitoring, Biomedical Engineering Letters, Feb. 2019, 16 pages, vol. 9.
Tavakolian, Characterization and Analysis of Seismocardiogram for Estimation of Hemodynamic Parameters, Simon Fraser University, Fall 2010, 217 pages.
Telfer, et al., Wearable Oximetry for Harsh Environments, IEEE, 2017, 4 pages.
Tilmanne, et al., Algorithms for sleep-wake identification using actigraphy: a comparative study and new results, European Sleep Research Society, Sep. 2008, 14 pages.
Tusman, et al., Photoplethysmographic characterization of vascular tone mediated changes in arterial pressure: an observational study, Journal of Clinical Monitoring and Computing, 2019, 10 pages, vol. 33.
Vetter, et al., Frequency Domain SpO2 Estimation Based on Multichannel Photoplethysmographic Measurements at the Sternum, IFMBE Proceedings, 2009, 4 pages, vol. 25.
Zakeri, et al., Analyzing Seismocardiogram Cycles to Identify the Respiratory Phases, IEEE Transactions on Biomedical Engineering, Aug. 2017, 7 pages, vol. 64 No. 8.
Zheng, et al., Low Ferfusion Algorithm used in Wearable Oximeter and Hardware Acceleration, IEEE, 2016, 5 pages.
Klum, et al., Wearable Cardiorespiratory Monitoring Employing a Multimodal Digital Patch Stethoscope: Estimation of ECG, PEP, LVET and Respiration Using a 55 mm Single-Lead ECG and Phonocardiogram, Sensors, Apr. 2020, 21 pages, vol. 20.
Semiz, et al., Non-Invasive Wearable Patch Utilizing Seismocardiography for Peri-Operative Use in Surgical Patients, IEEE, 2020, 11 pages.
Kwon, et al., Recent advances in wearable sensors and portable electronics for sleep monitoring, iScience, May 2021, 16 pages, vol. 24.
Ganti, et al., Wearable Cuff-less Blood Pressure Estimation at Home via Pulse Transit Time, IEEE Journal of Biomedical and Health Informatics, 2020, 12 pages.
Ha, et al., A Chest-Laminated Ultrathin and Stretchable E-Tattoo for the Measurement of Electrocardiogram, Seismocardiogram, and Cardiac Time Intervals, Advanced Science, 2019, 13 pages, vol. 6.
Jortberg, et al., a novel adhesive biosensor system for detecting respiration, cardiac, and limb movement signals during sleep: validation with polysomnography, Nature and Science of Sleep, 2018, 12 pages, vol. 10.
Javaid, et al., Quantifying and Reducing Motion Artifacts in Wearable Seismocardiogram Measurements during Walking to Assess Left Ventricular Health, IEEE TBME, 2017, 9 pages.
Morillo, et al., Monitoring and Analysis of Cardio Respiratory and Snoring Signals by using an Accelerometer, IEEE EMBS, Aug. 2007, 4 pages.
Solà, et al., On the reliability of pulse oximetry at the sternum, IEEE EMBS, Aug. 2007, 1 page.
"510(k) Premarket Notification." Accessdata.fda.gov, U.S. Department of Health & Human Services, Aug. 22, 2022, https://www.accessdata.fda.gov/scripts/cdrh/cfdocs/cfpmn/pmn.cfm?l.
FDA U.S. Food & Drug Administration. "Letter re: K213007, Trade/Device Name: Cerebra Sleep System . . . " Received by Cerebra Medical Ltd., Jul. 6, 2022, 17 pages.
U.S. Department of Health & Human Services. "Letter re: K162627, Trade/Device Name: EnsoSleep . . . " Received by EnsoData, Inc., Mar. 31, 2017, 7 pages.
FDA U.S. Food & Drug Administration. "Letter re: K210034, Trade/Device Name: EnsoSleep . . . " Received by EnsoData, Inc., May 2021, 24 pages.
Davies, Charles, et al., "A Single Arm, Open-Label, Multi-Center, and Comparative Study of the ANNE Sleep System versus Polysomnography to Diagnose Obstructive Sleep Apnea." Journal of Clinical Sleep Medicine : JCSM : Official Publication of the American Academy of Sleep Medicine, U.S. National Library of Medicine, https://pubmed.ncbi.nlm.nih.gov/35934926/.
Younes Sleep Technologies. "Traditional 510(k) Summary K112102 Michelle Sleep Scoring System." Oct. 16, 2011, 16 pages.
U.S. Department of Health & Human Services. "Letter re: K142988, Trade/Device Name: Sleepware G3 . . . " Received by Respironics, Inc., Mar. 16, 2015, 8 pages.
FDA U.S. Food & Drug Administration. "Letter re: K202142, Trade/Device Name: Sleepware G3 . . . " Received by Respironics, Inc., Oct. 29, 2020, 9 pages.

\* cited by examiner

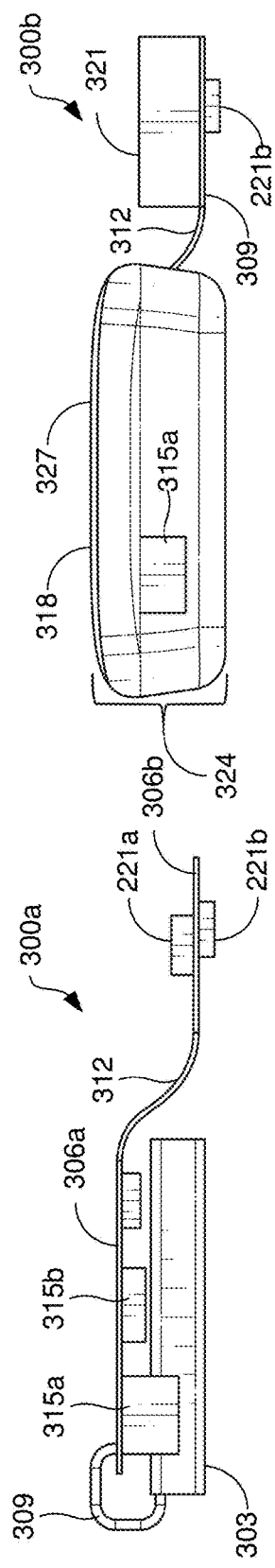
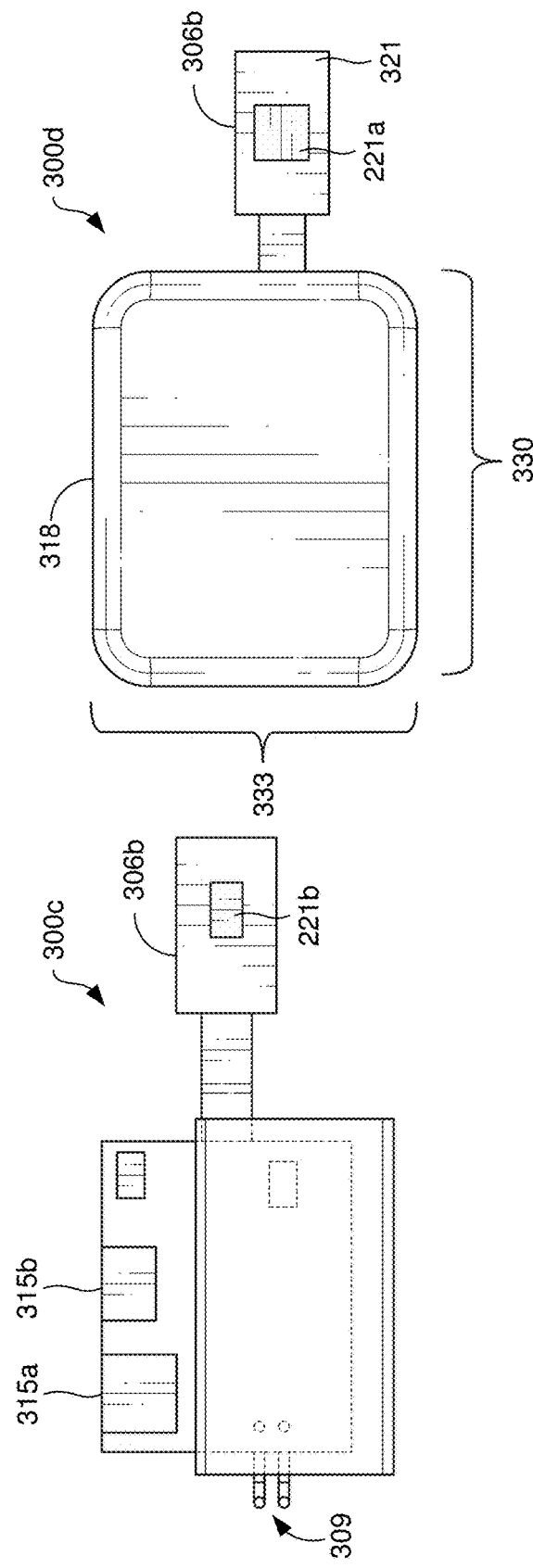
FIG. 3A
FIG. 3B
FIG. 3C
FIG. 3D

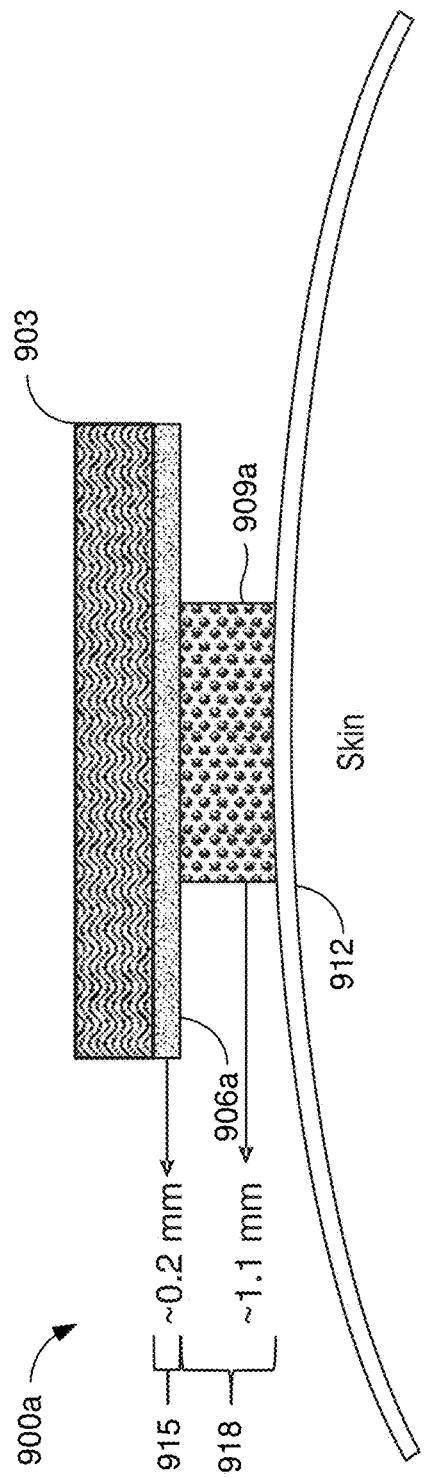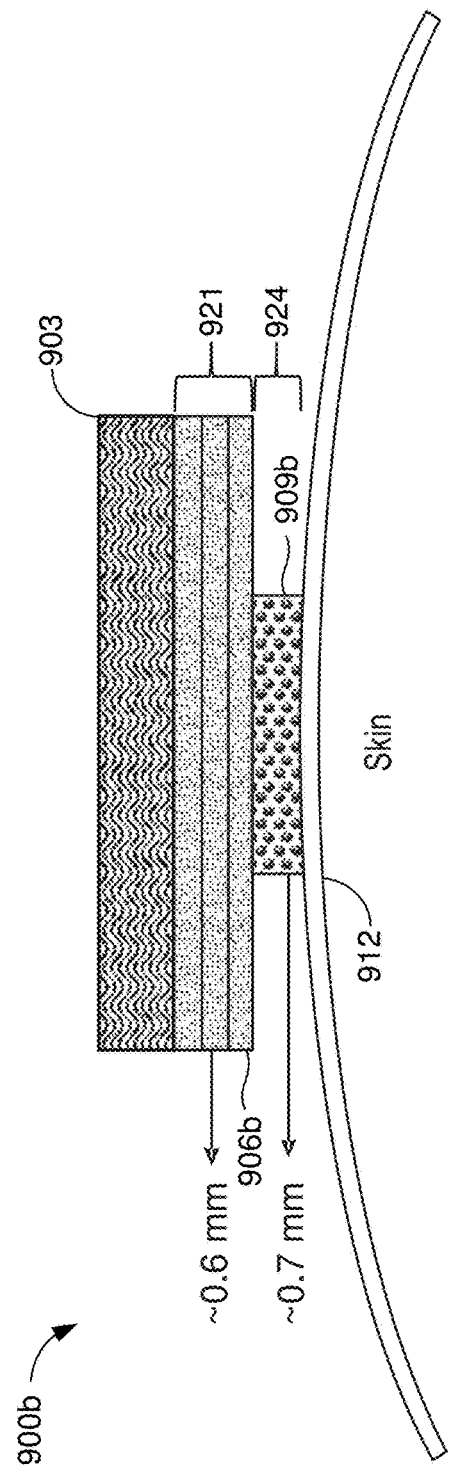
FIG. 9A
FIG. 9B

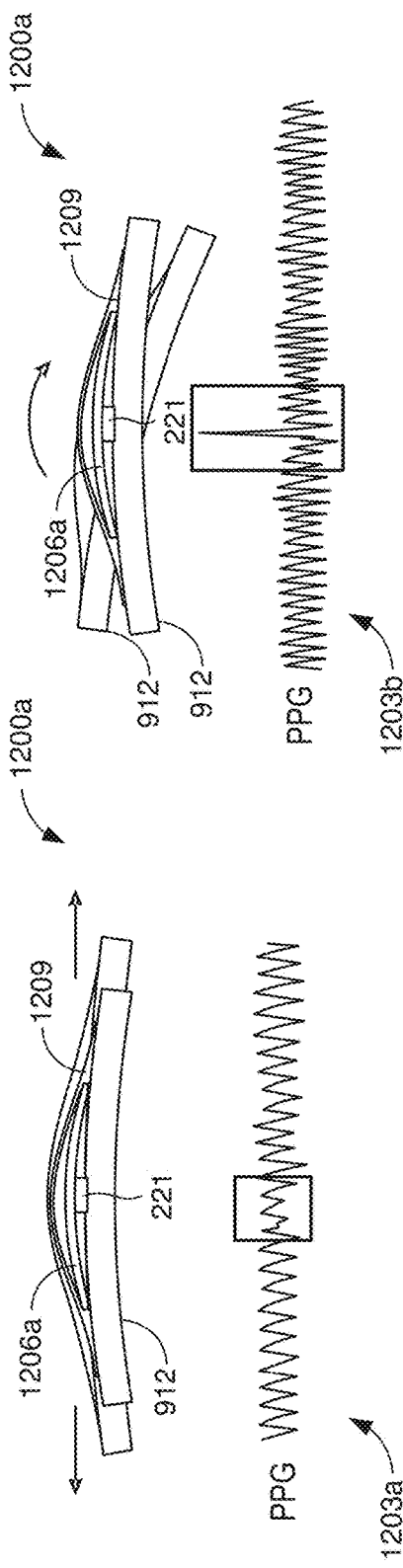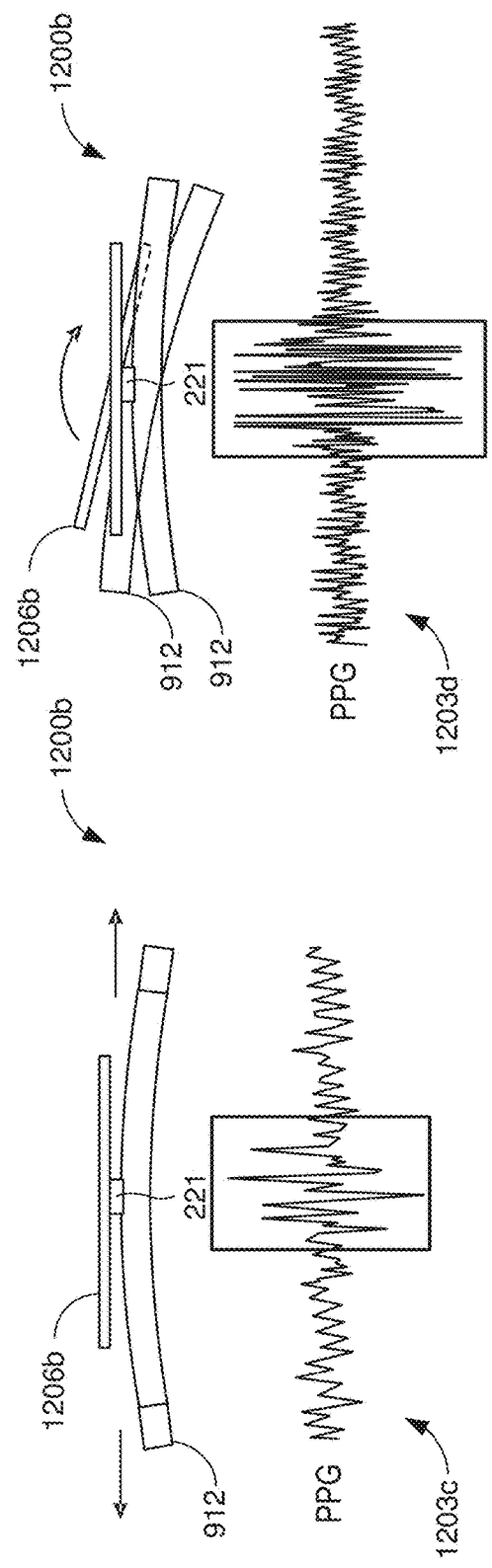

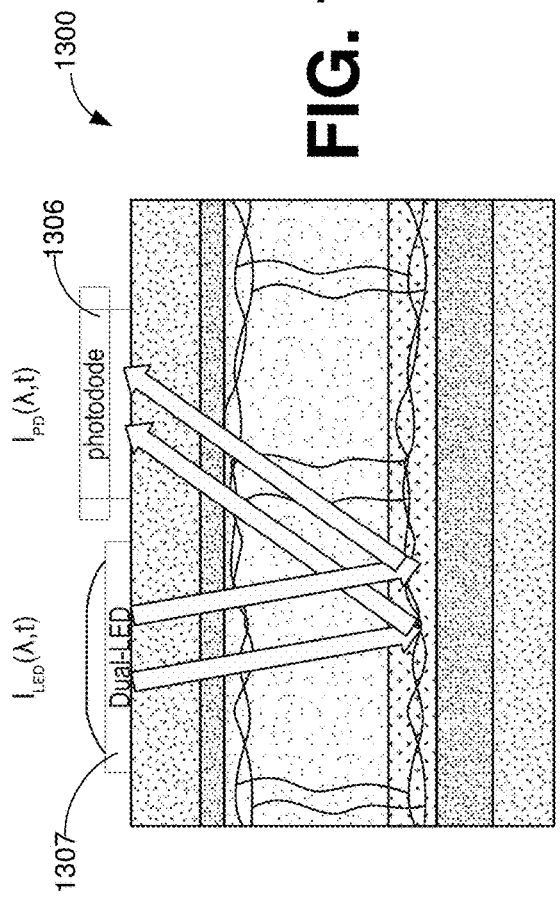
FIG. 13
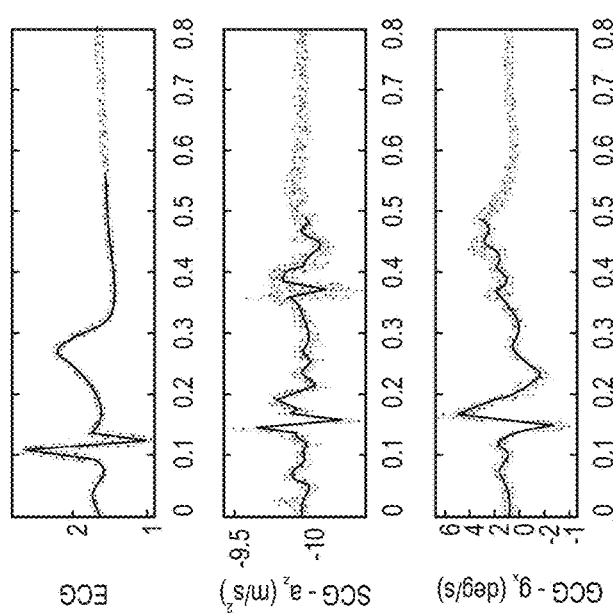
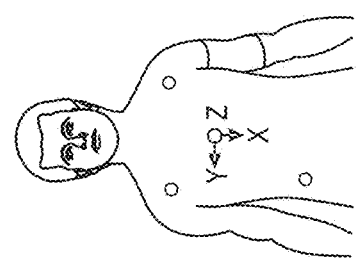
FIG. 14

PATCH FOR IMPROVED BIOMETRIC DATA CAPTURE AND RELATED PROCESSES

CROSS-REFERENCE TO RELATED APPLICATIONS

This application is a continuation of U.S. patent application Ser. No. 17/929,475, filed Sep. 2, 2022, entitled "PATCH FOR IMPROVED BIOMETRIC DATA CAPTURE AND RELATED PROCESSES," which is a division of U.S. patent application Ser. No. 17/199,181, filed Mar. 11, 2021, entitled "PATCH FOR IMPROVED BIOMETRIC DATA CAPTURE AND RELATED PROCESSES", which claims benefit of and priority to U.S. Provisional Patent Application No. 63/024,930, filed May 14, 2020, entitled "PATCH FOR IMPROVED BIOMETRIC DATA CAPTURE AND RELATED PROCESSES" and U.S. Provisional Patent Application No. 62/988,087, filed Mar. 11, 2020, entitled "PATCH AND PROCESSES FOR SAME," which are each incorporated herein by reference in their entirety.

BACKGROUND

Taking multiple types of measurements from a patient is typically a cumbersome process involving a number of sensors attached to various patient body parts. For example, in-clinic approaches for monitoring sleep-related disorders rely on a multitude of cumbersome devices and monitors. Even some home sleep tests include at least a finger pulse oximeter device for determining a patient's SpO2 levels, several belts for determining a patient's respiration effort, and a nasal cannula for determining respiration flow. Other types of home sleep tests include a clunky watch (worn on the wrist), a finger probe, and a snore sensor (worn on the chest).

Including a multitude of unconnected, separate devices placed on various locations of a patient's body can lead to a number of practical and technical issues. Using several separate devices (even if all are connected via wires) may lead to a high-probability of receiving poor quality or inaccurate sensor readings (e.g., if a patient rolls over and knocks off one of several sensors). Further, determining particular events may be difficult as integrating data from unconnected devices can be challenging as would be recognized by one of ordinary skill in the art. Such exemplary issues can lead to delayed or inaccurate diagnosis of, for example, sleep apnea. Further, the exemplary issues can prevent or delay a patient from using available testing apparatuses, even when done from a home, for fear it will disrupt or prevent them from losing further sleep.

Therefore, there is a long-felt but unmet need for systems, devices, and/or processes that can collect multiple patient measurements on a single device.

BRIEF SUMMARY

In various embodiments, the present disclosure provides patches (and processes for using the same) that monitor vasoconstrictions and other physiological phenomena associated with autonomic nervous system modulation. In at least one embodiment, the present patches perform both seismocardiography (SCG) and photoplethysmogram (PPG) measurements. According to one embodiment, the present patches and processes monitor PPG signals at performance levels superior to those demonstrated by transmission-type devices for monitoring PPG, such as, for example, digital pulse oximeters. In one or more embodiments, the present patches and processes are used for monitoring of sleep apnea and other sleep-related disorders based on readings of a plurality of factors including, but not limited to: 1) cardiac factors that are measured via a chest pulse oximeter; 2) oximetry that is measured using a chest pulse oximeter; 3) position and chest motion that are monitored via an accelerometer and/or gyroscope; 4) arousal level that is determined based on measured heart rate and seismocardiography computations; 5) actigraphy factors that are measured using a chest accelerometer; and 6) snoring that is measured using an ambient microphone.

Whereas previous approaches for monitoring sleep-related disorders rely on a multitude of cumbersome devices and monitors at a designated sleep clinic, in one or more embodiments, the low form factor of the present patches allows for monitoring of sleep-related disorders in a home setting and using a single device. In one example, previous approaches to PPG signal detection utilize an in-lab polysomnography (PSG) device that requires a multitude of complex belts, wires, probes, and other components be attached to various portions of a patient. In a contrasting example, an approach of the present disclosure includes securing a single multi-modal chest patch to a single portion of a patient. According to one embodiment, because the present patches include fewer distinct components compared to previous approaches, the patches herein demonstrate reduced technical failure risks and rates, and also demonstrate reduced time required to educate patients in their use of the sleep-monitoring device.

According to one aspect, a method including: providing a conformal patch device including a plurality of sensors configured to be positioned over a chest of a patient, the plurality of sensors including a photoplethysmography (PPG) sensor, an electrocardiogram (ECG) sensor, and an accelerometer sensor, wherein the conformal patch device is configured to adhere to a single continuous area, wherein at least one of the plurality of sensors is attached to a viscoelastic substrate to achieve mechanical strain isolation from other patch components; receiving, via at least one computing device, device registration information associated with the conformal patch device; capturing, via the conformal patch device, a plurality of sensor measurements from the plurality of sensors during a time window sufficient to detect disordered breathing; receiving, via the at least one computing device, the plurality of sensor measurements during the time window; and determining, via the at least one computing device, the disordered breathing and related cardiorespiratory parameters during the time window for the patient based on the plurality of sensor measurements.

According to another aspect, the method of this aspect or any other aspect, where the viscoelastic substrate includes at least one of: a composite of multiple materials, an elastic modulus in a range of 10-3000 MPa.

According to yet another aspect, the method of this aspect or any other aspect, where the viscoelastic substrate includes at least one of polyurethane, polyethylene and polyethylene teraphthalate (PET).

According to yet another aspect, the method of this aspect or any other aspect, where the viscoelastic substrate is geometrically patterned to relieve mechanical strain from at least one of the plurality of sensors.

According to yet another aspect, the method of this aspect or any other aspect, where a material, a pattern, an elastic modulus, a thickness, and a stiffness is specific to a region of the conformal patch device proximate to each of the plurality of sensors According to yet another aspect, the method of this aspect or any other aspect, further including providing, via the conformal patch device, a compressive downward force in a range of 0.5 and 2 Newtons on at least one of the plurality of sensors.

According to yet another aspect, the method of this aspect or any other aspect, further including computing a heart rate signal by measuring a signal via two electronic leads of the conformal patch device and performing threshold-based R-peak detection on the signal, wherein the cardiorespiratory parameters include the heart rate signal.

According to yet another aspect, the method of this aspect or any other aspect, further including affixing the conformal patch device to the chest of the patient by: positioning the conformal patch device over the chest of the patient; and contacting an adhesive surface on a first side of the conformal patch device to the chest of the patient.

According to yet another aspect, the method of this aspect or any other aspect, wherein the conformal patch device is positioned at one or more of an upper sternum, middle sternum, or mid-clavicle location on the chest of the patient.

According to yet another aspect, the method of this aspect or any other aspect, further including comparing a heart rate signal against a corresponding heart rate measurement device in real time to verify an accuracy of the conformal patch device.

According to yet another aspect, the method of this aspect or any other aspect, wherein the plurality of sensor measurements includes a heart rate measurement, a SpO2 measurement, a respiratory analysis, and a sleep time.

According to yet another aspect, the method of this aspect or any other aspect, wherein the plurality of sensors include an electrocardiogram (ECG) sensor, a chest pulse oximetry sensor, and at least one of an actimetry sensor and a heart rate variability (HRV) sensor.

According to yet another aspect, the method of this aspect or any other aspect, further including reprocessing the patch device by: wiping data from a memory storage of the patch device; cleaning the patch device; and returning the patch device to inventory for future use.

According to yet another aspect, the method of this aspect or any other aspect, further including comparing the heart rate signal against a corresponding heart rate measurement device in real time to verify an accuracy of the patch device.

According to yet another aspect, the method of this aspect or any other aspect, further including computing cardiorespiratory parameters by synchronously measuring the seismocardiogram via chest accelerometry and the electrocardiogram via at least two electrodes of the conformal patch, wherein the cardiorespiratory parameters include heart rate, heart rate variability, pre-ejection period, aortic valve opening magnitude, left ventricular ejection time, seismocardiogram fiducial timings and fiducial amplitudes.

According to yet another aspect, the method of this aspect or any other aspect, further including computing disordered breathing parameters by synchronously measuring the seismocardiogram and the respiratory tidal motions via chest accelerometry and the photoplethysmography-detected oxygen desaturations via at least one light emitting diode and one photodiode, wherein the disordered breathing parameters include obstructive sleep apnea, central sleep apnea, Cheyne-Stokes breathing, and chronic obstructive pulmonary disease.

According to one aspect, a patch system, including: a first adhesive layer; a PET layer; a silver layer; a silver/silver chloride layer; a conductive hydrogel layer; a dielectric layer; a printed circuit board layer including: a photoplethysmography (PPG) sensor mechanically isolated from other components, the PPG sensor including: an array board with a plurality of light emitting diodes (LEDs) individually alternated with individual ones of a plurality of photodiodes (PDs) to form an alternating array on the array board; and an adaptive filter configured to reduce a noise of readings from the plurality of PDs; and a seismocardiography (SCG) sensor including programmable digital filters; and at least one computing device including a hardware processor and in communication with the PPG sensor and the SCG sensor, the at least one computing device configured to: receive a plurality of measurements from each of the PPG sensor and the SCG sensor; and determine disordered breathing and related cardiorespiratory parameters during a time window based on the plurality of measurements; and a second adhesive layer configured to adhere to a single continuous area of a skin of a patient.

According to another aspect, the patch system of this aspect or any other aspect, wherein the at least one computing device is further configured to capture a respective time stamp for each of the plurality of measurements and store the plurality of measurements associated with the respective time stamp.

According to yet another aspect, the patch system of this aspect or any other aspect, further including a power source circuit configured to provide a power signal to the PPG sensor, the SCG sensor, and the at least one computing device.

According to yet another aspect, the patch system of this aspect or any other aspect, wherein the power source circuit includes: a battery; a battery recharge circuit configured to receive an external power signal and store power from the external power signal in the battery; a load circuit configured to: provide power from the battery when the battery recharge circuit is not receiving the external power signal; and provide an input power signal from the external power signal when the battery recharge circuit is receiving the external power signal; and at least one power regulator coupled to the load circuit, the at least one power regulator configured to modify a voltage of the input power signal to provide the external power signal to the PPG sensor, the SCG sensor, and the at least one computing device.

According to yet another aspect, the patch system of this aspect or any other aspect, wherein the PPG sensor further includes: the second adhesive layer coupled to the array board; and a sensor depth control feature coupled to the second adhesive layer.

According to yet another aspect, the patch system of this aspect or any other aspect, wherein: the sensor depth control feature includes a length and a width smaller than a length and a width of the second adhesive layer; and the adhesive layer is configured to contact a skin of an individual around a periphery of the sensor depth control feature.

According to yet another aspect, the patch system of this aspect or any other aspect, wherein a surface area of the patch system configured to contact the skin of the patient includes less than 10 square inches.

According to yet another aspect, the patch system of this aspect or any other aspect, wherein the second adhesive layer includes a thickness of between 0.5 millimeter and 0.7 millimeters.

According to yet another aspect, the patch system of this aspect or any other aspect, wherein the at least one computing device is further configured to compute a respiratory-induced frequency variation based on measurements from the PPG sensor.

According to yet another aspect, the patch system of this aspect or any other aspect, further including a gyroscope, an accelerometer, a compass, and a digital motion processor configured to offload computation of motion processing algorithms from the at least one computing device.

According to yet another aspect, the patch system of this aspect or any other aspect, further including a radio frequency filter coupled to at least one computing device and an antenna coupled to the radio frequency filter.

According to yet another aspect, the patch system of this aspect or any other aspect, wherein the at least one computing device is further configured to communicate with the PPG sensor and the SCG sensor via an I2C bus.

According to yet another aspect, the patch system of this aspect or any other aspect, wherein a quality of signals measured from the PPG sensor and the SCG sensor is based on a flexibility and stretchability of a material of a component coupling the patch system to a chest of an individual.

According to yet another aspect, the patch system of this aspect or any other aspect, wherein the at least one power regulator includes a 1.8v regulator and a 3.3v regulator.

According to yet another aspect, the patch system of this aspect or any other aspect, wherein the SCG sensor includes three SCG sensors and the PPG sensor includes two PPG sensors.

According to yet another aspect, the patch system of this aspect or any other aspect, wherein the PPG sensor further includes: an adhesive layer; a foam layer coupled to the adhesive layer; a flexible circuit layer coupled to the foam layer, wherein the PPG sensor is positioned against a central portion of the flexible circuit layer; and an elastomer interface layer adjacent to the flexible circuit layer, wherein the elastomer interface layer and the PPG sensor are configured to contact.

According to yet another aspect, the patch system of this aspect or any other aspect, wherein the plurality of light emitting diodes (LEDs) and the plurality of photodiodes (PDs) pass into a sensor depth control feature.

According to yet another aspect, the patch system of this aspect or any other aspect, wherein the adhesive layer includes T1503 adhesive.

According to yet another aspect, the patch system of this aspect or any other aspect, wherein the adhesive layer includes a plurality of adhesive layers.

According to yet another aspect, the patch system of this aspect or any other aspect, wherein the sensor depth control feature includes a thickness of approximately 0.7 millimeters.

According to yet another aspect, the patch system of this aspect or any other aspect, further comprising: a plurality of copper layers separated by a plurality of insulative layers; and an elastomeric insulation layer.

According to yet another aspect, the patch system of this aspect or any other aspect, wherein the PPG sensor is configured to sense vasoconstriction, heart rate, and SpO2 levels.

According to yet another aspect, the patch system of this aspect or any other aspect, wherein a respective spacing between alternating ones of the plurality of LEDs and the plurality of PDs includes between 6 and 12 millimeters.

According to yet another aspect, the patch system of this aspect or any other aspect, wherein the respective spacing includes at least one of 6 millimeters, 9 millimeters, or 12 millimeters.

According to yet another aspect, the patch system of this aspect or any other aspect, further comprising a microphone configured to monitor audio generated by a chest of an individual.

According to yet another aspect, the patch system of this aspect or any other aspect, wherein the microphone includes a pulse-density modulated microphone.

According to yet another aspect, the patch system of this aspect or any other aspect, further comprising a data port and a storage device coupled to the at least one computing device, wherein the at least one computing device is further configured to: store the plurality of measurements to the storage device; and transmit the plurality of measurements from the storage device to an external computing device via the data port.

According to yet another aspect, the patch system of this aspect or any other aspect, further comprising an electrocardiogram (ECG) amplifier.

According to yet another aspect, the patch system of this aspect or any other aspect, wherein the at least one computing device is further configured to compute a respiratory-induced amplitude variation based on measurements from the PPG sensor.

According to yet another aspect, the patch system of this aspect or any other aspect, wherein the at least one computing device is further configured to compute at least one of a respiratory-induced frequency variation based on measurements from the PPG sensor, tidal movements, actigraphym, SCG fiducial timing, SCG fiducial amplitude.

According to yet another aspect, the patch system of this aspect or any other aspect, further comprising a pulse oximeter and a heart-rate sensor.

According to yet another aspect, the patch system of this aspect or any other aspect, wherein the at least one computing device is further configured to: receive a plurality of packets from at least one of the PPG sensor and the SCG sensor; and verify at least one of a cyclic redundancy check (CRC), a checksum, or a parity associated with the plurality of packets.

According to one embodiment, a patch device, including: a first adhesive layer; a PET layer; a silver layer; a silver/silver chloride layer; a conductive hydrogel layer; a dielectric layer; a printed circuit board layer including: a photoplethysmography (PPG) sensor including: an array board with a plurality of light emitting diodes (LEDs) individually alternated with individual ones of a plurality of photodiodes (PDs) to form an alternating array on the array board; and an adaptive filter configured to reduce a noise of readings from the plurality of PDs; and a seismocardiography (SCG) sensor including an analog to digital converter and a three axis sensor; at least one computing device including a hardware processor and in communication with the PPG sensor and the SCG sensor, the at least one computing device configured to: receive a plurality of measurements from each of the PPG sensor and the SCG sensor; and determine disordered breathing and related cardiorespiratory parameters during a time window based on the plurality of measurements; and a second adhesive layer configured to adhere to a single continuous area of a skin of a patient.

According to another aspect, the patch device of this aspect or any other aspect, wherein the patch device includes a rectangular prism shape with a size of between 11 and 16 millimeters deep by between 42 and 47 millimeters long by between 32 and 37 millimeters wide.

According to yet another aspect, the patch device of this aspect or any other aspect, further including a digital signal processor circuit and an analog to digital converter circuit.

According to yet another aspect, the patch device of this aspect or any other aspect, wherein the plurality of measurements describe at least one analog waveform.

According to yet another aspect, the patch device of this aspect or any other aspect, wherein the at least one computing device is further configured to: identify an amplitude of a signal from the PPG sensor; determine that the amplitude of the signal exceeds a predetermined threshold; and in response to the amplitude exceeding the predetermined threshold, generate an indication that the patch device is improperly applied to a chest of an individual.

According to yet another aspect, the patch device of this aspect or any other aspect, wherein the amplitude corresponds to at least one of a red signal or an infrared signal.

According to yet another aspect, the patch device of this aspect or any other aspect, further including a plurality of sensors including a gyroscope, an accelerometer, a compass, wherein the at least one computing device is further configured to the disordered breathing and the related cardiorespiratory parameters via chest accelerometry based on the plurality of sensors.

According to yet another aspect, the patch device of this aspect or any other aspect, wherein the at least one computing device is further configured to determine inertial measures of thoracoabdominal movement, wherein the cardiorespiratory parameters are determined based on the inertial measures of the thoracoabdominal movement.

According to yet another aspect, the patch device of this aspect or any other aspect, wherein the at least one computing device is further configured to: measure, via the PPG sensor, cutaneous blood flow and volume; and determine blood oxygen saturation (SpO2) derived from the cutaneous blood flow and volume.

According to yet another aspect, the patch device of this aspect or any other aspect, wherein the at least one computing device is further configured to determine heart rate variability based on measurements from the PPG sensor, the SCG sensor, and an electrocardiogram (ECG) sensor.

According to yet another aspect, the patch device of this aspect or any other aspect, wherein the at least one computing device is further configured to communicate sensor data via Bluetooth with at least one external device.

According to yet another aspect, the patch device of this aspect or any other aspect, wherein the rectangular prison includes between 17 and 22 millimeters deep by between 50 and 55 millimeters long by between 34 and 39 millimeters wide.

According to yet another aspect, the patch device of this aspect or any other aspect, wherein the at least one computing device is further configured to: identify at least one missing data portion on the storage device; and identify the storage device for replacement based on the at least one missing data portion.

According to yet another aspect, the patch device of this aspect or any other aspect, wherein the at least one computing device is further configured to: communicate with an external service to determine that a new firmware version is available; download the new firmware version and store the new firmware version on a local storage device; verify a signature corresponding to the new firmware version; and in response to the signature being verified, execute the new firmware version.

According to yet another aspect, the patch device of this aspect or any other aspect, wherein the at least one computing device is further configured to: transfer measurement data to an external device; in response to the measurement data being transferred, perform a data wipe by actively writing to a flash memory to permanently erase the measurement data.

According to yet another aspect, the patch device of this aspect or any other aspect, wherein the plurality of measurements describe at least one analog waveform.

According to yet another aspect, the patch device of this aspect or any other aspect, wherein the PPG sensor is configured to perform dual-depth sensing comprising sensing superficial tissue and sensing deeper vessel tissue.

According to yet another aspect, the patch device of this aspect or any other aspect, wherein the patch device is configured to adhere to a single continuous area of a chest.

According to yet another aspect, the patch device of this aspect or any other aspect, wherein the single continuous area includes a sternum or a clavicle.

BRIEF DESCRIPTION OF THE EXHIBITS

FIGS. 3A-3D illustrate patch devices according to various embodiments of the present disclosure.

FIGS. 9A and 9B illustrate patch devices according to various embodiments of the present disclosure.

FIGS. 12A-12D illustrate patch devices with corresponding signals according to various embodiments of the present disclosure.

FIG. 13 illustrates a cross-sectional view of a dual LED and PD sensing system of a patch device according to various embodiments of the present disclosure.

FIG. 14 illustrates example sensor measurements from a patch device according to various embodiments of the present disclosure.

DETAILED DESCRIPTION

Using technology to diagnose conditions for a patient can be challenging and require sensor measurements from various types of sensors. Moreover, a patient's movements while measurements are being taken can lead to inaccurate or inconsistent data. While patients may be asked to not move, some limited patient movement is inevitable. The movement may be amplified and unpreventable if the time window for capturing the data includes sleeping for all or a portion of the time. In addition, the sensors themselves may disrupt or prevent sleeping by an individual. When each sensor is placed in a different location or connected to a different lead, sleeping may be even more challenging. In addition, it can be challenging for a patient to fall asleep when in a clinical setting.

The disclosed patch device can provide a singular continuous area of contact to collect various sensor measurements. The patch device can include various flexible and stretchable materials to provide for consistent and accurate measurements from the various sensors when the patient moves or if/when forces are applied to the patch device. The patch device can also be used within a home of the patient, which is more convenient and can provide for a better sleep experience. Sensing cardiorespiratory parameters in a natural sleep environment (e.g., a bed of a patient in the patient's residence) can prevent introducing new sleep disruption symptoms that may result in an inaccurate diagnosis. The patch device may also include local power and data storage to allow a patient to sleep without being connected to external devices. The locally stored data can be retrieved from the data storage after the testing window is completed. In some embodiments, and as further discussed herein, the disclosed patch may be remotely connected to one or more external or remote systems or transmitting and/or analyzing data.

Figure 1:
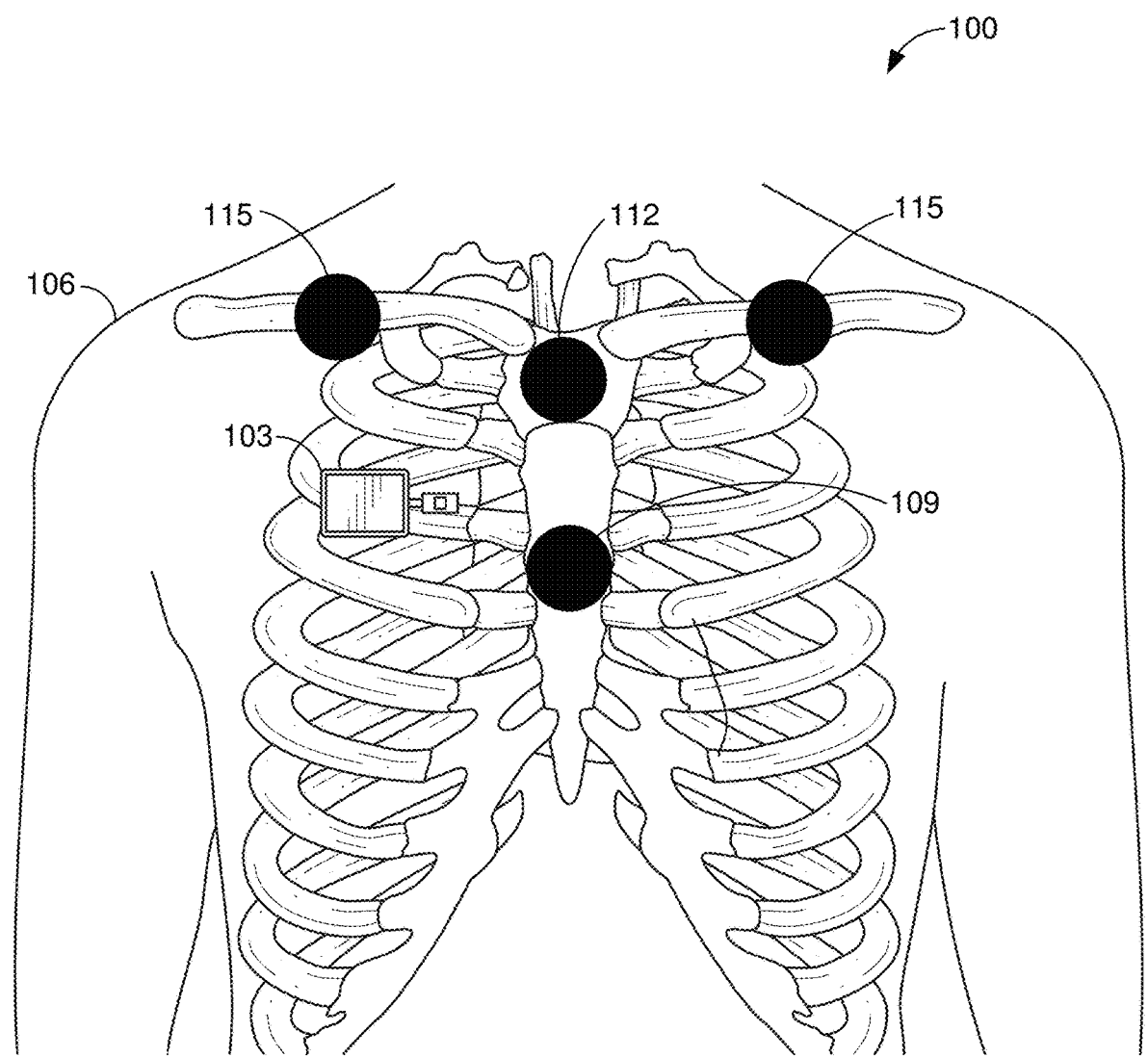
FIG. 1 illustrates a sensing environment according to various embodiments of the present disclosure.

Turning to FIG. 1, shown is a sensing environment 100 according to various embodiments of the present disclosure. The sensing environment 100 can include a patch device 103 positioned on a chest of an individual 106. The patch device 103 can be a conformal patch with one or more sensors embedded therein. The patch device 103 can include an adhesive to affix the patch device 103 onto a chest of the individual 106. As an example, the patch device 103 can be applied to the skin of the individual 106 at a position on the chest.

The sternum may have an upper sternum 112, a lower sternum, and a middle sternum 109. The position on the chest of the individual 106 that the patch device 103 can be applied to may be the middle sternum 109, the upper sternum 112, and/or the mid-clavicle 115. The middle sternum 109 may be the middle 50% of the sternum. The middle sternum 109 may have a mid-point that is a half-way point between a first end and a second end of the sternum, or near (e.g., within 5%, within 10%, within 15%) the half-way point of the sternum. The middle sternum 109 may also be an area around the mid-point of the middle sternum 109. The area around the mid-point of the sternum may be defined as a circular area with a radius in which the mid-point of the middle sternum 109 is the center point of the circular area. The radius of the circular area may be, but is not limited to, 0.1 inches, one inch, two inches, four inches, six inches, or any other measurement. The size of the area (e.g., circular or other shaped area) may be, but is not limited to, 0.1 square inches, one square inch, two square inches, four square inches, six square inches, ten square inches, less than 10 square inches, or any other measurement. For example, patch device 103 may be within the circular area around the mid-point of the middle sternum 109.

The upper sternum 112 may be a top (e.g., top 25%, top 10%, top 5%, etc) of the sternum of a user. The upper sternum 112 may also be an area around a mid-point of the upper sternum 112. The upper sternum 112 may have a mid-point that is at a half-way point of the upper sternum 112 (e.g., at or near the top 12.5% point of the sternum). The area around the mid-point of the upper sternum 112 may be defined as a circular area with a radius in which the mid-point of the upper sternum 112 is the center point of the circular area. The radius of the circular area may be, but is not limited to, 0.1 inches, one inch, two inches, four inches, six inches, or any other measurement.

The mid-clavicle 115 may be an area around a middle portion of the user's clavicle. The clavicle extends from the sternum to the shoulder. The middle portion of the user's mid-clavicle 115 may have a mid-point that is the half-way point on the clavicle between the sternum and the shoulder. The area around the mid-point of the mid-clavicle 115 may be defined as a circular area with a radius in which the mid-point of the mid-clavicle 115 is the center point of the circular area. The radius of the circular area may be, but is not limited to, 0.1 inches, one inch, two inches, four inches, six inches, or any other measurement. The patch device 103 can include one or more flexible layers to conform to the skin of the chest. In some embodiments, the sensors can be attached to a viscoelastic substrate to mechanically isolate the sensors from the other aspects of the patch device 103 (e.g., such that when a patient moves, resulting forces affect the substrate and not necessarily the mechanically isolated sensors). This viscoelastic substrate can include an adhesive area for contact with the skin of the patient. The adhesive area can facilitate the sensors maintaining contact with the skin of the individual when the individual moves or when pressure is applied to the patch device 103. As an example, an individual may unconsciously or consciously toss and turn during a sleeping session, which may cause forces to be applied to the patch device 103. Those forces may pull or push on various areas of the patch device 103, which may cause movement of the sensors relative to the skin of the individual. The adhesive area combined with the flexible layers of the patch device 103 can facilitate the sensors to maintain constant contact with the skin when the patient is moving.

In some embodiments, the patch device 103 can be used for diagnosis of one or more disorders or identifying one or more concerns or parameters, such as sleep apnea, disordered breathing, and other cardiorespiratory parameters. The patch device 103 can be provided to a user or patient to test for a disorder or to collect measurements for evaluation by a physician. Once received, the user can register the patch device 103 with a testing service. The patch device 103 can be applied to the chest of an individual, also referred to herein as a test subject, patient, and user. Once applied to the chest (or prior to application to the chest in some embodiments), collection of sensor data may be initiated. As an example, the patch device 103 may receive an input such as receiving a button push or a wireless message to start collecting data. The patch device 103 can continue collecting data and storing the data locally (or transmitting the data to a remote computing device) until a predetermined time expires, a subsequent input is received, or a particular event is detected. The particular event can include determining that a patient has stopped breathing, determining that the patient has woken up from a sleep, identifying a condition, determining that a patients vitals are within a normal range or outside of a normal range, or some other event.

The patch device 103 can capture measurements from sensors in the patch device 103 over a period of time. The patch device 103 can store the measurements locally (e.g., on local storage/memory). In some embodiments, the patch device 103 can process raw measurements to calculate or compute measurement-based data, and store the measurement-based data. As an example, the patch device 103 can compute a heart rate, a breathing rate, a SpO2 level, and other vital signs using raw sensor measurements, and store these measurement-based data items on the local storage. In some embodiments, the patch device 103 can capture measurements and store information about the individual during a sleep window to determine if and when the patient is sleeping. The system can diagnose or provide data to a physician for a diagnoses that the individual has or does not have sleep apnea, disordered breathing, and other cardiorespiratory parameters. As will be understood from discussions herein, the patch device 103 may also send all raw signal data to a separate or remote computing system for analysis (e.g., in at least one embodiment, the patch device 103 does not compute any measurements). The patch device 103 can be positioned on an upper sternum 112 or a mid-clavicle 115 on the chest of the patient.

Figure 2:
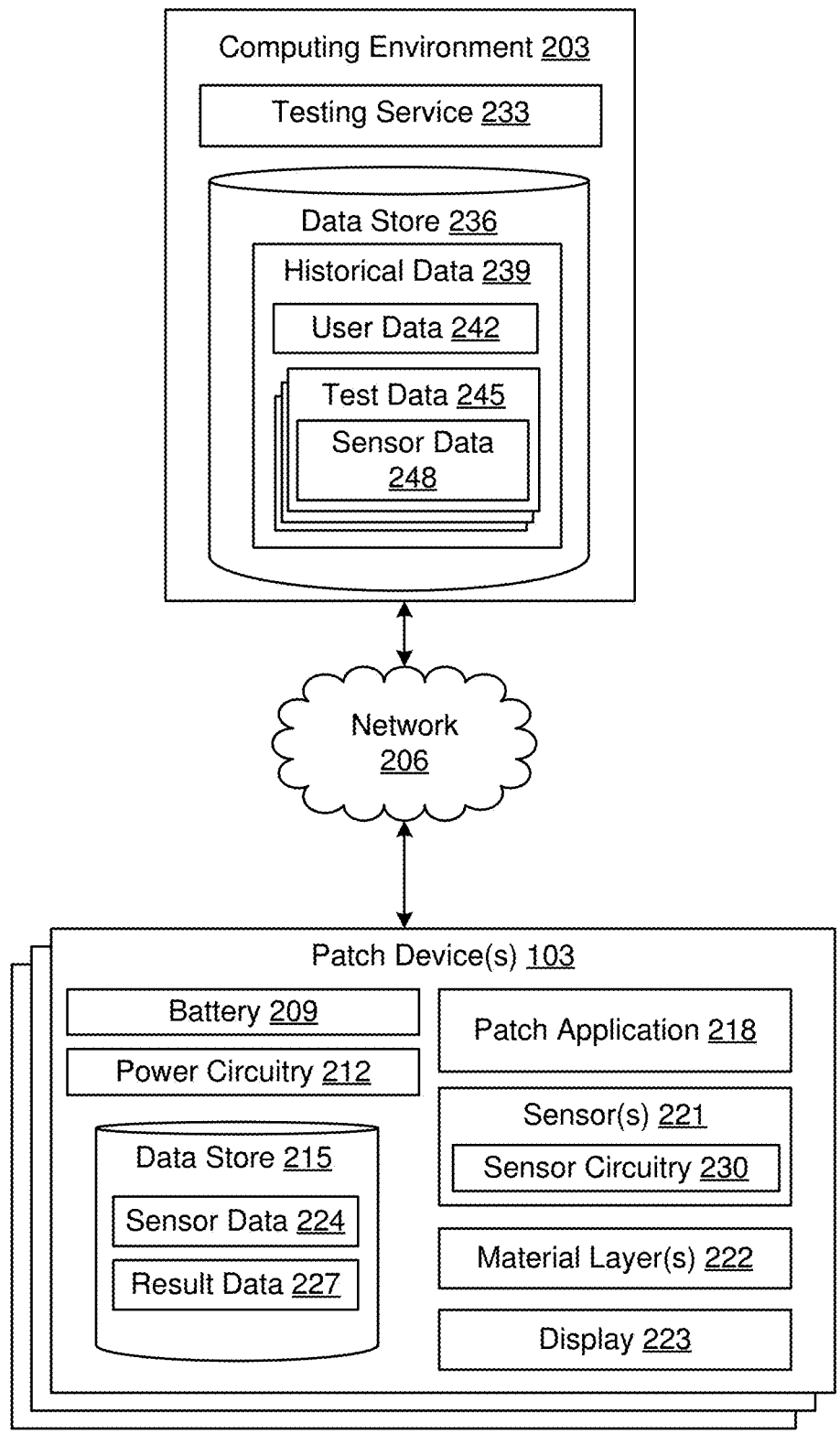
FIG. 2 illustrates a sensing environment according to various embodiments of the present disclosure.

FIG. 2 shows a sensing environment 200 according to various embodiments of the present disclosure. In some embodiments, the sensing environment 200 can be a sensing environment 100 as shown in FIG. 1. The sensing environment 200 includes a computing environment 203, and one or more patch devices 103, which are in data communication with each other via a network 206. The network 206 includes, for example, the Internet, intranets, extranets, wide area networks (WANs), local area networks (LANs), wired networks, wireless networks, or other suitable networks, etc., or any combination of two or more such networks. For example, such networks can include satellite networks, cable networks, Ethernet networks, Bluetooth networks, Wi-Fi networks, LoRaWAN network, NFC networks, and other types of networks.

The patch device 103 can be coupled to the network 206. The patch device 103 can include, for example, one or more batteries 209, one or more power circuitries 212, one or more data stores 215, a patch application 218, one or more sensors 221, and one or more material layers 222. The patch device 103 can include, for example, a processor-based system such as a computer system. In one embodiment, patch device 103 can include a display 223. The display 223 can include, for example, one or more devices such as liquid crystal display (LCD) displays, gas plasma-based flat panel displays, organic light emitting diode (OLED) displays, electrophoretic ink (E ink) displays, LCD projectors, or other types of display devices, etc.

The patch device 103 can be configured to execute various applications such as a patch application 218 and/or other applications. The patch application 218 is configured to be executed by patch device 103. The patch application 218 can correspond to one or more firmware components or an image configured to run on a computing device or other components of the patch device 103 to perform various functionality described herein. As an example, the patch application 218 can be executed by a computing device to read from the sensors 221, store data in the data store 215, and communicate via the network 206 to the computing environment 203 (e.g., with the testing service 233) or other software components.

The patch application 218 can communicate with an external service (e.g., the testing service 233) over the network to determine that a new firmware version is available. The patch application 218 may determine a new firmware version is available on an storage device (e.g., in data store 215, a USB flash drive, etc.). The patch application 218 can download the new firmware version and store the new firmware version on a local storage device (e.g., data store 215). The patch application 218 can transfer or copy over the new firmware version to the data store 215 from a flash drive or other external storage. Before installing the new firmware image, the patch application 218 can verify the new firmware version, such as, for example, by verifying a signature corresponding to the new firmware version. Verifying the signature can include ensuring a digital signature was signed by a trusted certificate authority. The digital signature can be verified using a public key of the trusted certificate authority. Verifying the signature can include ensuring an integrity of the data (e.g., making sure the data is not corrupted), such as by verifying a checksum, hash, or CRC of the firmware image. In response to the signature being verified, the patch application 218 can install the new firmware version and/or execute the new firmware version. In some embodiments, once the new firmware version is installed, the patch application 218 reboots the computing device to automatically execute the new patch application 218 installed from the new firmware version.

The sensors 221 may include various types of sensors, for example, a photoplethysmography (PPG) sensor, an electrocardiogram (ECG) sensor, a seismocardiography (SCG) sensor, an accelerometer sensor, or any other similar sensors including those sensors discussed herein. The patch application 218 can receive the sensor measurements from the sensors 221 and determine health parameters (e.g., cardiorespiratory parameters, disordered breathing parameters, etc.) from the sensor measurements. The cardiorespiratory parameters may include respiratory effort derived from inertial measures of thoracoabdominal movement, heart rate, heart rate variability, pre-ejection period, aortic valve opening magnitude, left ventricular ejection time, seismocardiogram fiducial timings and fiducial magnitudes, optical measures of cutaneous blood flow and volume, and blood oxygen saturation (SpO2) derived from optical measures of blood flow via the PPG sensor 221, heart rate and heart rate variability derived from the ECG, PPG, and/or SCG sensors 221, respiratory rate derived from inertial measures of thoracoabdominal movement, PPG sensors 221, and/or SCG sensors 221. The health parameters indicating disordered breathing or health issues may include obstructive sleep apnea, central sleep apnea, Cheyne-Stokes breathing, and chronic obstructive pulmonary disease.

The battery 209 and the power circuitry 212 may be operatively connected as a power source circuit to provide power the patch device 103. The battery 209 may be a power source for the patch device 103. The battery may receive an external power signal from an external power source via the power circuitry 212 and store the external power signal to charge the battery. The power circuitry 212 may include a battery recharge circuit and/or a load circuit. The battery recharge circuit may receive an external power signal and store power from the external power signal in the battery.

The load circuit may provide power from the battery to the patch device 103. The load circuit may provide power from the battery when the battery recharge circuit is not receiving the external power signal. The load circuit may also provide an input power signal from the external power signal. The load circuit may provide the input power signal from the external power signal when the battery recharge circuit is receiving the external power signal (e.g., when the battery is charging via the external power source via the battery recharge circuit, the external power source may also be providing power to the patch device 103 via the load circuit). The load circuit may also be coupled to at least one power regulator. The power regulator may be configured to modify a voltage of the input power signal to provide the external power signal to the data store 215, patch application 218, and/or sensors 221. The at least one power regulator may include a 1.8v regulator and a 3.3v regulator, or other similar regulators.

The data store 215 may store various types of data, for example, sensor data 224, result data 227, and other similar data types. Sensor data 224 may include sensor measurements taken by the sensors 221. As can be appreciated, sensor measurements as described herein can correspond to individual measurements over time or an analog data signal such as a biosignal (e.g., a heartbeat signal). In some embodiments, analog data signals can be stored as a time series of discrete values. In one embodiment, the analog data signals can include one or more frequency, and the time series of discrete values can be captured at a frequency of at least twice the highest frequency of each analog data signal (e.g., greater than the Nyquist frequency) such that each analog data signal can be losslessly recreated. In other embodiments, a data value (e.g., heartbeat) may be extracted from an analog signal by a sensor 221 and/or the patch application 218, and the data value may be stored as the sensor measurement (e.g., either as a discrete value or a time series of discrete values). The sensor data 224 can include a respective timestamp for each sensor measurement. The sensor data 224 can also include an identifier and/or type associated with the type of sensor 221 from which the measurement was derived. The sensor data 224 can include a firmware version being executed while collecting each measurement, hardware version of the sensor circuitry 230, hardware version of other hardware components on the patch device 103, and other information.

The data store 215 can store sensor data 224, such as measurements from each sensor 221 serially over time as an array, vector, queue, or other data format. The measurements can be stored such that each type of measurement can be traversed chronological. The measurements may each be traversed together as a group chronologically. For example, the patch application (or testing service 233) can read a PPG measurement, an ECG measurement and an SCG measurement from a first time, and then read a second PPG measurement, a second ECG measurement, and a second SCG measurement from a second time with the second time being chronologically after the first time. In one embodiment, the second time is one second after the first time. In another embodiment, the second time is 10 milliseconds after the first time. The patch application 218 can iterate chronologically through the measurements from all types of sensors 221 together. The measurements can be stored in a format that can be read by the patch application 218 or exported to the data store 236 and read by the testing service 233.

The sensors 221 may be operatively connected with the patch application 218. The sensors may communicate with the patch application 218. The sensors 221 may capture measurements (as discussed herein) from a patient and transmit the sensor measurements for processing. In at least one embodiment, the sensors 221 transmit measurements to the patch application 218 to be stored in the data store 215, the patch application 218 may process the data in real time or process from the data store 215 to determine whether disordered breathing and related cardiorespiratory parameters are occurring based on the sensor measurements among other collected data. According to some embodiments, the sensors 221 transmit measurements to a radio (or other suitable computing component on the patch device 103 for transmission to a remote computing device for analysis).

In some embodiments, the testing service 233 may receive the sensor measurements and determine whether disordered breathing and related cardiorespiratory parameters are occurring by analyzing the sensor measurements among other collected data. The sensors 221 may capture a certain amount of sensor measurements (e.g., 10 sensor measurements, 50, 100, etc.) over a certain amount of time (e.g. one minute, one hour, eight hours) and/or capture sensor measurements at a certain time interval (e.g., one measurement per second, one measurement per minute, etc.).

In some embodiments, the sensors 221 include sensor circuitry 230 that can capture multiple sensor measurements and transmit the sensor measurements to the patch application 218 in bulk. A frequency of capturing each sensor measurement can be based on feedback from previous measurements (e.g. a current heart rate or SpO2 rate), types of data being measured (e.g. expected range of times of an occurrence (e.g., a heartbeat)). The patch application 218 can configure a specified number of measurements each sensor 221 may take. For example, a sensor 221 may detect and capture each heartbeat of a user over a specified amount of time or a sensor 221 may take a certain quantity of sensor measurements (e.g., set by the system, user, etc.).

A PPG sensor 221 (e.g., via the patch application 218 or by itself) can monitor and measure a user's heart rate. In some embodiments the heart rate can be measured by an ECG sensor 221. In one embodiment, a measurement from the PPG sensor 221 can be compared to a measurement by the ECG sensor 221 to verify an accuracy. In another embodiment, multiple sensors 221 can capture and determine a same vital statistic (e.g., a heart rate) such that if a particular sensor 221 reads incorrect data (e.g., because the particular sensor 221 shifted, was pushed, was bumped, encountered sweat or water, etc.) the measured vital statistic from another one of the multiple sensors 221 can be used instead until the particular sensor 221 is fixed or reads correctly.

The PPG sensor 221 may measure volumetric variations of blood circulation at the surface of the user's skin via optics. The PPG sensor 221 may perform reflectance-mode photoplethysmorgram signal detection of a design and sampling range of 50-200 Hz. The PPG sensor may be configured to monitor, measure, and/or sense sensor measurements, such as, but not limited to, vasoconstriction, heart rate, SpO2 levels, cutaneous blood flow and volume. The patch device 103 may apply a compressive downward force to the PPG sensor. In one embodiment, the compressive downward force may be in the range of 0.5-2.0 Newtons.

The PPG sensor 221 can include an array board with a plurality of light emitting diodes (LEDs) and a plurality of photodiodes (PDs). The array board may include alternating individual LEDs and PDs on the array board such that each individual LED is proximate to individual PDs, and each individual PD is proximate to individual LEDs. For example, the array board can include a printed circuit board (PCB) with pairs of apertures for leads of a PD or an LED spaced a part at a specific distance. The specific distance may be greater than or equal to 6 mm, 6 mm, 9 mm, 12 mm, or some other distance as can be appreciated. The PPG sensor 221 may include an adaptive filter configured to reduce a noise of readings from the plurality of PDs. The adaptive filter can be applied to a measurement or signal from the PPG sensor 221 and/or the ECG sensor 221 to extract information using frequency-domain or time-domain features. As an example, the adaptive filter can extract beat-to-beat heartbeats from a data signal corresponding to the PPG sensor 221 and/or the ECG sensor 221.

The ECG sensor 221 can read, monitor, and measure electrical activity (e.g., voltage) of a patient's heart over time (among other things). The ECG sensor may detect a heartbeat or other electrical properties of the heart via the voltage changes in the user's heart. The ECG sensor 221 may also include an electrocardiogram (ECG) amplifier. In some embodiments, the ECG sensor 221 can include a two-lead, a three-lead or other number of lead ECG sensor.

An SCG sensor 221 can obtain seismocardiogram (SCG) signals that can be used to compute respiratory measurements such as a respiration rate and chest acceleration. The SCG sensor 221 may detect, monitor, and/or measure sensor measurements such as patient heart rate, respiration rate, and other metrics associated with diagnosis, monitoring, and/or treatment of sleep-related disorders. The SCG sensor 221 may include an accelerometer and/or a gyroscope to compute the respiratory measurements. The SCG sensor 221 may include a 3-axis accelerometer and/or 3-axis gyroscope of a design sampling range specified within the attached data (150-500 Hz). In various embodiments, the patch device 103 demonstrates less signal quality degradation (e.g., SNR) to the seismocardiogram (SCG) signal caused by patient snoring vibrations and patient bodily movements due to one or more of: 1) the specific placement location on the torso as defined within the attached data; 2) application of digital filtering techniques; and 3) device adhesion configurations as defined within the present disclosure (e.g., see FIGS. 9-12). The use of SCG-based components and processes reduces a count of components and a bulk of components used to perform sleep-monitoring of a patient (e.g., as compared to counts and bulks of components utilized in previous approaches). The SCG sensor 221 may include programmable digital filters.

The sensors 221 may also include sensor circuitry 230. For some sensors 221, the sensor circuitry 230 can include one or more digital signal processors (DSP) to process signals measured by the sensor 221. In some embodiments, the computing device executing the patch application 218 can include one or more DSPs to process signals from the sensors 221. The sensor circuitry 230 can include a digital motion processor or other hardware processor and/or memory device. The processor can offload computation of motion processing algorithms from the computing device (e.g., computing device 703 in FIG. 7). The hardware processor can process the signal from the sensor 221 using one or more DSPs to extract various data measurements. The data measurements and/or the signal can be stored in a memory of the sensor circuitry 230. The data measurements can be stored in a buffer or queue that is continuously or in batch transmitted to the patch application 218.

One or more material layers 222 can be included in the patch device. For example, the material layers may provide protection for the battery 209, power circuitry 212, data store 215, patch application 218, and/or sensors 221 in the patch device 103. The material layers 222 may include one or more adhesive layers, one or more viscoelastic layers, one or more flexible circuit layers, one or more elastomer interface layers. In some embodiments, the layers may have different materials at different portions. As an example, a first material can be used for a particular layer 222 while a second material can surround a sensor 221 within that particular layer 222. The material layers 222 may also include copper layers and insulative layers among other materials. The material layers 222 may also include an elastomeric insulation layer. The copper layers and insulative layers may be alternated to prevent signals from crossing between copper layers except where vias are included.

In some embodiments, some of the layers 222 of a material may be stacked or layered along a first axis, while other layers 222 may represent an area occupying an area or volume of space (e.g., around a sensor). In some embodiments, two or more material layers 222 may occupy a common position along the first axis with different positions on the other axes. For example, two or more layers 222 may be adjacent to one another in a same plane. As another example, a foam layer 222 may surround a surface of a sensor 221 (e.g., foam portion 321 in FIG. 3) and the sensor 221 may include one or more material layers 222 on the surface of the sensor 221 (e.g., an adhesive layer 222 or filter layer 222).

The sensors 221 may be attached to a viscoelastic substrate layer 222 to achieve mechanical isolation from the other patch device 103 components. As will be understood from discussions herein, certain sensors (e.g., PPG, ECG) may produce better (e.g., higher amplitude) or more consistent signals when adhered or pressed against the chest (even when a chest expands/contracts and/or a patient rolls during sleep) and thus it is advantages for these sensors to be coupled to a flexible/stretchable substrate and otherwise be isolated from rigid components, such as for example, a circuit board.

The viscoelastic substrate layer 222 may include a one or more materials, for example, polyurethane, polyethylene, polyethylene terephthalate (PET), and/or other similar materials. The viscoelastic substrate may include an elastic modulus in the range of 10-3000 MPa. The viscoelastic substrate layer 222 may include a stiffness of 10 to 500 Newtons per meter (N/m). The viscoelastic substrate layer 222 may be geometrically patterned to relieve strain from at least one of the sensors 221. The viscoelastic substrate layer 222 may include a high percentage (e.g., greater than 80% surface area) of adhesive area across the sensors 221 configured to maintain sensor contact with a patient's skin. In some embodiments, the viscoelastic substrate layer 222 may include a window or area omitting adhesive for the sensor 221 to contact the skin. As an example, the viscoelastic substrate layer 222 may have adhesive at all parts except for an area corresponding to the sensor 221. The area corresponding to the sensor 221 that omits adhesive can correspond to less than 20% of surface area of the viscoelastic substrate layer 222. The viscoelastic substrate layer 222 may have a certain thickness. The material, geometric pattern, elastic modulus, stiffness, and thickness of the viscoelastic substrate layer 222 may be specific to a region of the patch device 103 proximate to each of the sensors 221.

The computing environment 203 can include, for example, a server computer or any other system providing computing capability. Alternatively, the computing environment 203 can employ more than one computing devices that can be arranged, for example, in one or more server banks or computer banks or other arrangements. Such computing devices can be located in a single installation or can be distributed among many different geographical locations. For example, the computing environment 203 can include one or more computing devices that together can include a hosted computing resource, a grid computing resource and/or any other distributed computing arrangement. In some cases, the computing environment 203 can correspond to an elastic computing resource where the allotted capacity of processing, network, storage, or other computing-related resources can vary over time.

Various applications and/or other functionality can be executed in the computing environment 203 according to various embodiments. The computing environment 203 can include a testing service 233 and a data store 236. Also, various data is stored in a data store 236 that is accessible to the computing environment 203. The data store 236 can be representative of one or more of data stores 236 as can be appreciated. The data stored in the data store 236 for example, is associated with the operation of the various applications and/or functional entities described below.

The data stored in the data store 236 includes, for example, historical data 239, and potentially other data. Historical data 239 may include user data 242, test data 245, and other similar types of data. The test data may further include sensor data 248. The historical data 239 can include data from one or more tests or monitoring sessions performed by one or more patch devices 103. When a patch device 103 collects data for a patient over a time window, the data can be transferred over the network 206 and stored in test data 245. The sensor data 244 and result data 227 can be stored in test data 245 and sensor data 248 indexed based on a variety of information (e.g., patient identifier, patch device identifier, one or more properties associated with the test results, etc.). For example, the test data 245 can be indexed by whether a patient associated with user data 242 was diagnosed with a condition (e.g., sleep apnea) or other properties of the test result such that a search of test data 245 could surface all tests that involve a particular diagnosis, condition, arrhythmia, problem, or other property.

The user data 242 can include patient information for one or more patients that use the patch device 103 or are treated by one or more physicians. The test service 233 can receive the data from one or more patch devices 103 and store the data in the data store 236. In some embodiments, a user or patient may access the testing service 233 via a URL for a website and register the patch device 103 for use in a test or collection period. The user can provide patient information via the URL, which the testing service 233 can track in user data 242. The user data 242 can include authentication information, such as credentials including multi-factor credentials for logging in to access test information and updating registration. The testing service 233 can provide test results captured by one or more patch devices 103 via a user interface to one or more users once authenticated. The user interfaces can provide a history of tests performed as well as potentially analytics, diagnoses, and potentially other information.

With reference to FIG. 3A, shown is an example patch device 300a according to various embodiments of the present disclosure. In one embodiment, the patch device 300a can be a patch device 103 as described herein. The patch device 300a can include a first portion 303 coupled to a first rigid printed circuit board (PCB) 306a via a conductive material 309, and a second rigid PCB 306b coupled to the first rigid PCB 306a via a flexible conductive material 312.

In some embodiments, the first portion 303 can include a battery or other power circuitry. The power can be provided via the conductive material 309. In one example, the conductive material can include two conductors. In one embodiment, the two conductors carry a positive and negative power signal from the battery to the first rigid PCB 306a. In another embodiment, the conductive material 309 can include a data bus to carry information from the first PCB 306a to circuitry in the first portion 303. The first portion 303 can include power recharge circuitry to power other circuits and recharge a power level of the battery.

The first rigid PCB 306a and/or the second PCB 306b can include one or more connectors 315a and 315b, and one or more sensors 221, such as sensors 221a and 221b. In one example, the connector 315a can be a Japan Solderless Terminal (JST) connector and the connector 315b can be a Universal Serial Bus (USB) connector. In another example, the sensor 221a can be an accelerometer and the sensor 221b can be a PPG sensor. One of the first portion 303, the first rigid PCB 306a, and the second rigid PCB 306b can include a computing device that executes the patch application 218 (FIG. 2) and is in communication with the connectors 315a and 315b and the sensors 221a and 221b.

The flexible conductive material 312 can carry power and data signals between the first rigid PCB 306a and the second rigid PCB 306b. The flexible conductive material 312 can partially mechanically decouple the first rigid PCB 306a from the second rigid PCB 306b. As an example, some movements (e.g, within a limited range of movements) of the first rigid PCB 306a can result in flexing of the flexible conductive material 312 without moving the second rigid PCB 306b (and vice versa). As one example, the first PCB 306a and the second PCB 306b can be adhesively affixed to a skin of a patient, and the first PCB 306a and the second PCB 306b may flex with respect to one another when the patient moves or breaths or if a pressure is applied (e.g., the patient itches or pushes on) to one of the first PCB 306a or the second PCB 306b.

With reference to FIG. 3B, shown is an example patch device 300b according to various embodiments of the present disclosure. The example patch device 300b can correspond to the patch device 300a with the addition of a case 318 and a foam portion 321. In one embodiment, the case 318 can have a depth 324 of 14 millimeters (mm). In another embodiment, the case can have a depth 323 of 19.8 mm.

The foam portion 321 can be covered in an adhesive to couple to a skin of the patient. The adhesive may be an over-adhesive that compresses the foam portion 321 to normally load the PPG sensor 221a. An adhesive can also couple a top surface 327 of the case 318 to a skin of the patient. In some embodiments, the PPG sensor 221a can include a height substantially equal to a height of the foam so that the PPG sensor 221a can adhesively contact the skin of the patient to measure one or more types of measurements as are described herein.

With reference to FIG. 3C, shown is an example patch device 300c according to various embodiments of the present disclosure. The example patch device 300c can correspond to the patch device 300a as viewed from a bottom angle.

With reference to FIG. 3D, shown is an example patch device 300d according to various embodiments of the present disclosure. The example patch device 300d can correspond to the patch device 300b as viewed from a top angle. A sensing surface of the PPG sensor 221A\a can be coplanar with a surface of the foam portion 321 configured to contact with the skin of the patient. In one embodiment, a length 330 of the case 318 can be 45 mm and a width 333 of the case 318 can be 35 mm. In another embodiment, a length 330 of the case 318 can be 52.5 mm and a width 333 of the case 318 can be 36.5 mm.

Figure 4A:
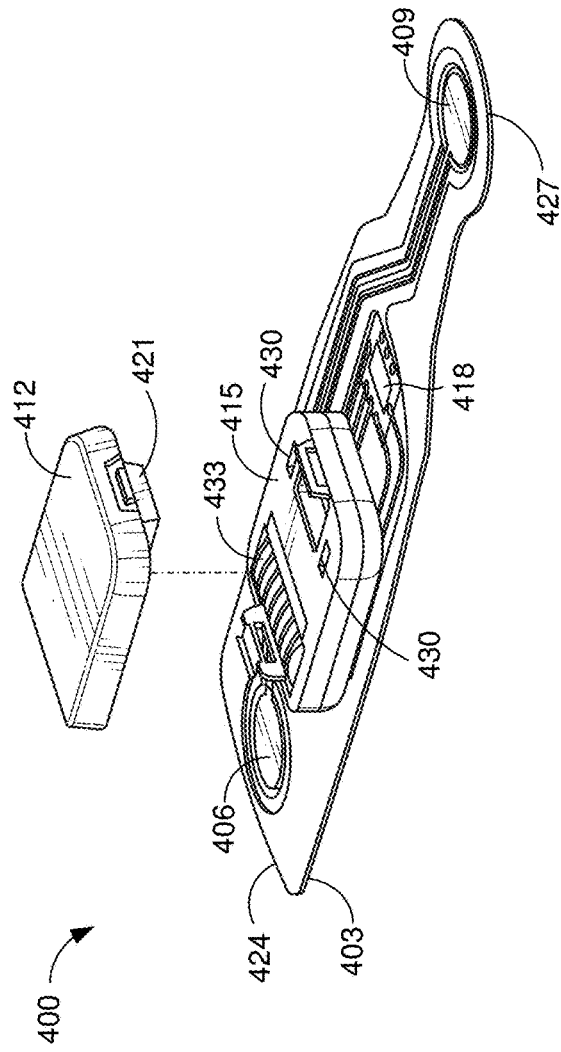
FIG. 4A illustrates a top perspective view of a patch device according to various embodiments of the present disclosure.

With reference to FIG. 4A, shown is a top perspective view of an example patch device 400, according to various embodiments of the present disclosure. In one embodiment, the patch device 400 can be a patch device 103 as described herein. The patch device 400 can include a flexible circuit layer 403, which may include a bottom adhesive layer, a first ECG electrode 406, a second ECG electrode 409, a receptacle cover 412, a battery receptacle 415, a PPG sensor layer 418, and/or an accelerometer 421. One of the bottom adhesive layer 403, receptacle cover 412, and the battery receptacle 415 can include a computing device that executes the patch application 218 (FIG. 2) and is in communication with the ECG electrode 406, the second ECG electrode 409, PPG sensor layer 418, and accelerometer 421. In various embodiments, the receptacle cover 412, battery receptacle 415, accelerometer 421, and battery (see FIG. 5) may be detachable from the flexible circuit layer 403. In some embodiments, the flexible circuit layer 403, the first ECG electrode 406, the second ECG electrode 409, and/or the PPG sensor layer 418 may be disposable. In another embodiment, the patch device 400 may be disposable. In yet another embodiment, an adhesive layer may be disposable and the flexible circuit layer may be reusable.

In some embodiments, the receptacle cover 412 or the battery receptacle 415 can include a battery or other power circuitry. The power can be provided by the battery via flexible circuit layer 403. In one embodiment, the flexible circuit layer 403 carries a positive and negative power signal from the battery to the ECG electrode 406, the second ECG electrode 409, PPG sensor layer 418, and accelerometer 421. In another embodiment, the flexible circuit layer 403 can include a data bus to carry information from the computing device to the ECG electrode 406, the second ECG electrode 409, PPG sensor layer 418, and/or accelerometer 421. The ECG electrode 406, the second ECG electrode 409, PPG sensor layer 418, and accelerometer 421 can be powered by the battery via the flexible circuit layer 403.

In certain embodiments, the flexible circuit layer 403 can provide equivalent functionality as PCB 306a, shown in FIG. 3. The flexible circuit layer 403 can have a bottom surface that contacts the user's skin, and a top surface that contacts other components of the patch device 400, such as the ECG electrode 406, the second ECG electrode 409, PPG sensor layer 418, and accelerometer 421. The flexible circuit layer 403 can include different types of layers, such as, but not limited to, one or more adhesive layers, one or more foam layers, a flexible circuit layer, one or more copper layers, one or more silver layers, one or more a silver/silver chloride layers, one or more conductive hydrogel layer, one or more insulative layers (e.g., polyimide dielectric layers), and/or one or more elastomeric insulation layers. In at least one embodiment, the one or more copper layers, one or more silver layers, one or more silver/silver chloride layers, and/or the one or more conductive hydrogel layers may be conductive so that the flexible circuit layer 403 may include circuit traces to implement circuits, such as those described in FIGS. 7 and 8 as well as positive and negative power signal from the battery to the sensors, and carry information to and from the sensors. The silver/silver chloride layer may be utilized as part of the ECG sensor and/or other sensors by delivering current to the ECG sensor and/or other sensors. The conductive hydrogel layer may be polymer chains that contain conductive properties viscoelastic properties so that the conductive hydrogel layer may be used in connection with an individual's skin. The conductive hydrogel layer can improve the conductivity of electrodes in the flexible circuit layer 403 and patch device 400. In one embodiment, the flexible circuit layer 403 may include a thickness of between 0.5 millimeters and 0.7 millimeters. The flexible circuit layer 403 may have a first end 424 and a second end 427.

The bottom surface of the flexible circuit layer 403 can include an adhesive that contacts and adheres the user's skin so that the patch device 400 is connected to the user. The adhesive on the bottom surface of the flexible circuit layer 403 may be a medical adhesive. The adhesive on the bottom surface of the flexible circuit layer 403 may be T1503 adhesive.

In some embodiments, sensors 221, as discussed in relation to FIG. 2 may include the first ECG electrode 406 and the second ECG electrode 409. The first ECG electrode 406 and the second ECG electrode 409 may have a circular shape with a certain diameter, such as, but not limited to, 15 to 25 millimeters.

In multiple embodiments, the receptacle cover 412 may, along with the battery receptacle 415, cover the battery. The receptacle cover 412 may have a bottom surface, a top surface, and one or more side surfaces. In certain embodiments, the receptacle cover 412 may enclose the battery and a portion of the power circuitry. In some embodiments, the battery receptacle 415 may enclose the battery and a portion of the power circuitry. The receptacle cover 412 and the battery receptacle 415 may be electrically coupled via battery contacts 430 and board connections 433.

The accelerometer 421 may be operatively attached to the receptacle cover 412. The accelerometer can be attached to any surface of the receptacle cover 412. In another embodiment, the accelerometer 421 may be operatively connected to the battery receptacle 415. The accelerometer 421 is electrically coupled to the receptacle cover 412, which is electrically coupled to the battery receptacle 415 via the battery contacts 430 and board connections 433. The board connections 433 may include a data bus to carry information from the computing device to and from the accelerometer via the flexible circuit layer 403.

The PPG sensor layer 418 may include a PPG sensor (of the sensors 221), which may be an array board with a plurality of LEDs and a plurality of PDs, and PPG sensor circuitry. The PPG sensor layer 418 may be generally square or rectangular-shaped.

The flexible circuit layers 403 can include multiple layers, such as, but not limited to, one or more adhesive layers, one or more foam layers, one or more elastomer interface layers, one or more flexible circuit layers, one or more copper layers, one or more insulative layers (e.g., plastic dielectric layers), and/or one or more elastomeric insulation layers. The flexible circuit layers 403 can also include electrical components, such as, but not limited to, a PPG sensor (e.g., PPG sensor 706 in FIG. 7A) (an array board with LEDs and PDs on the array board), and conductive material.

A bottom elastomeric insulation skin adhesion layer may include one or more adhesive layers or include one or more adhesive layers and an elastomeric insulation layer. The bottom elastomeric insulation skin adhesion layer may include T1503 adhesive.

The flexible circuit layers 403 may also include a sensor depth control feature coupled to the bottom elastomeric insulation skin adhesion layer. The plurality of LEDs and PDs on an array board (e.g., array board 600 in FIG. 6) may pass into the sensor depth control feature. The space may include a length and width smaller than the length and width of the bottom elastomeric insulation skin adhesion layer, such that the bottom elastomeric insulation skin adhesion layer is configured to contact a user's skin around a periphery of the sensor depth control feature. The bottom elastomeric insulation skin adhesion layer may have a thickness of between 0.5 and 0.7 millimeters. The bottom elastomeric insulation skin adhesion layer may include a plurality of adhesive layers.

In various embodiments, the patch device 103 may include one or more foam layers above the flexible circuit layer. The one or more foam layers can provide protection for the flexible circuit layer while maintaining the flexibility of the patch. The one or more foam layers protect the flexible circuit layer by providing insulation and a barrier for the electrical components when the patch is handled by users. In at least one embodiment, the one or more foam layers may have a thickness between 5 mm and 25 mm.

The patch device 103 can include an adhesive layer over one or more foam layers to facilitate attachment of the one or more foam layers to additional patch components (e.g., a patch covering). The adhesive layer over the one or more foam layers may facilitate attachment of the patch to the human body. The adhesive layer may be a medical adhesive. The adhesive layer over the one or more foam layers may provide a compression force on the flexible substrate circuit board such that a normal load is applied to the PPG sensor, thus improving the signal quality of the PPG sensor. The PPG sensor may be positioned against or proximate to the center point of the flexible circuit layer. The PPG sensor may also include an elastomer interface layer adjacent to the flexible circuit layer, such that the elastomer interface layer and the PPG sensor are configured to contact. A quality of signals measured by the sensors (e.g., the PPG sensor and the SCG sensor) can be directly related to and based on the flexibility and stretchability of a material of material layers (e.g., material layers 222 from FIG. 2) adjacent to the sensor 221 and to the layer coupling the patch device 103 to a chest of an individual.

In addition to the advantages described above, in at least one embodiment, the present disclosure includes a patch with a minimized air gap between skin of patient and a circuit board to minimize stress concentrations on a patient and rotation of the patch (thereby potentially increasing signal amplitude and consistency of signal readings).

Figure 4B:
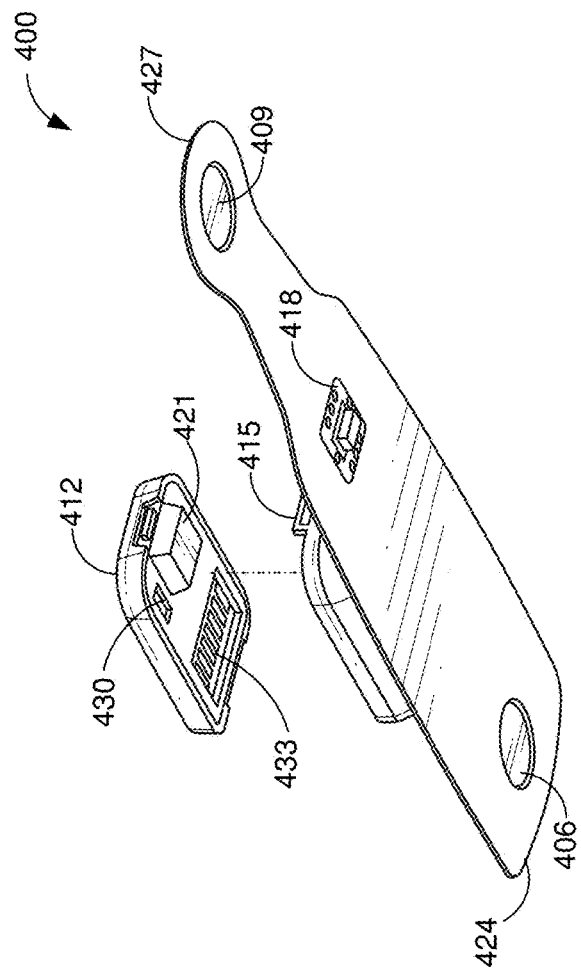
FIG. 4B illustrates a bottom perspective view of a patch device according to various embodiments of the present disclosure.

With reference to FIG. 4B, shown is a bottom perspective view of an example patch device 400, according to various embodiments of the present disclosure. The flexible circuit layer 403 may define a first opening proximate to the first end 424 of the flexible circuit layer 403, and may define a second opening proximate to the second end 427 of the flexible circuit layer 403. Each of the first opening and second opening may have a certain diameter. The diameter of each of the first opening and second opening may be less than or equal to the diameter of the first ECG electrode 406 and the second ECG electrode 409. The first ECG electrode 406 may be placed in the middle of the first opening, and the second ECG electrode 409 may be placed in the middle of the second opening so that the first ECG electrode 406 and the second ECG electrode 409 may directly access the user's skin (e.g., there may be no layers between the first ECG electrode 406 and the user's skin, and there may be no layers between the second ECG electrode 409 and the user's skin).

The flexible circuit layer 403 may also define a third opening that is shaped so that the PPG sensor layer 418 may directly access the user's skin (e.g., there may be no layers between the PPG sensor layer 418 and the user's skin).

Figure 5:
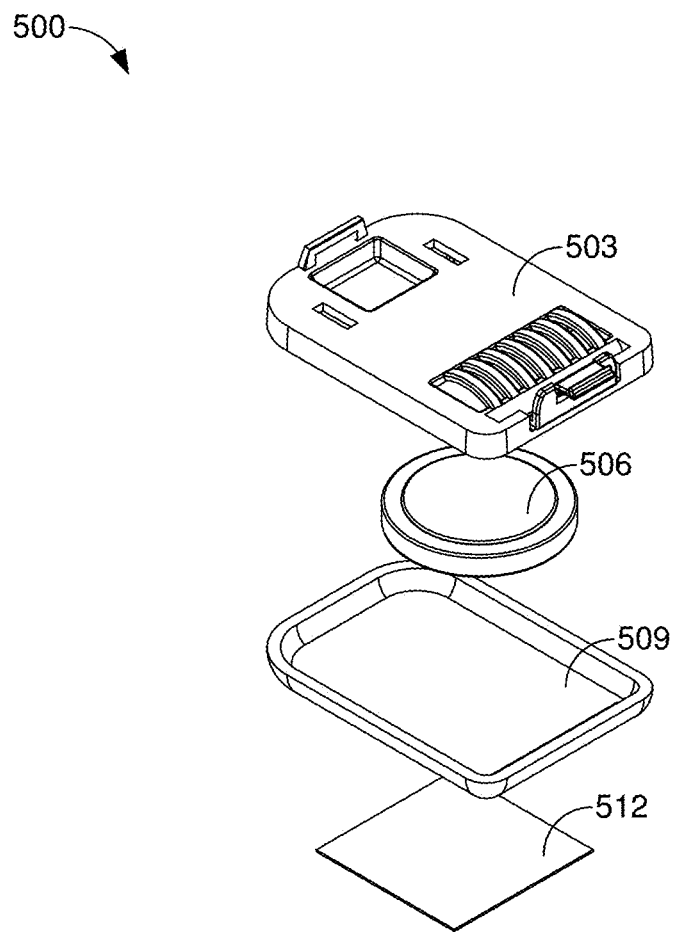
FIG. 5 illustrates an exploded view of a battery receptacle according to various embodiments of the present disclosure.

With reference to FIG. 5, shown is an exploded view of an example battery receptacle 500, according to various embodiments of the present disclosure. In one embodiment, battery receptacle 500 can be a battery receptacle 415 as described herein. The battery receptacle 500 may include a battery cover 503, a battery 506, a battery tray 509, and a PSA receptacle 512. The battery cover 503, a battery 506, a battery tray 509, and a pressure sensitive adhesive (PSA) receptacle 512 may be welded together, or otherwise operatively connected.

The battery cover 503 may define a square or rectangular-shaped opening for receiving the accelerometer 421 or a portion of the accelerometer 421. In one embodiment, the battery cover 503 may have dimensions of 30-40 millimeters in length by 20-30 millimeters in width by 2-10 millimeters in height. The battery cover may be made of polycarbonate-ABS, or some other similar material.

In some embodiments, the battery 506 can be the battery 209. The battery 506 may be connected to power circuitry, such as power circuitry 212. The battery 506 may be enclosed by the battery cover 503 and the battery tray 509. In one embodiment, the battery 506 may be a 3V battery.

The battery tray 509 can receive the battery 506. The battery tray 509 and the battery cover 503 may operatively connect to enclose the battery. The battery tray may be made of polycarbonate-ABS or other similar materials. The battery tray 509 may have the same or similar length and width dimensions as the battery cover 503. The battery tray 509 may have dimensions of 30-40 millimeters in length, 20-30 millimeters in width, and 2-5 millimeters in height.

The PSA receptacle 512 may operatively connect to the battery tray 509 and an adhesive layer, such as the flexible circuit layer 403, flexible circuit layer, and/or a PCB layer, such as PCB 306*a* and/or PCB 306*b*.

Figure 6:
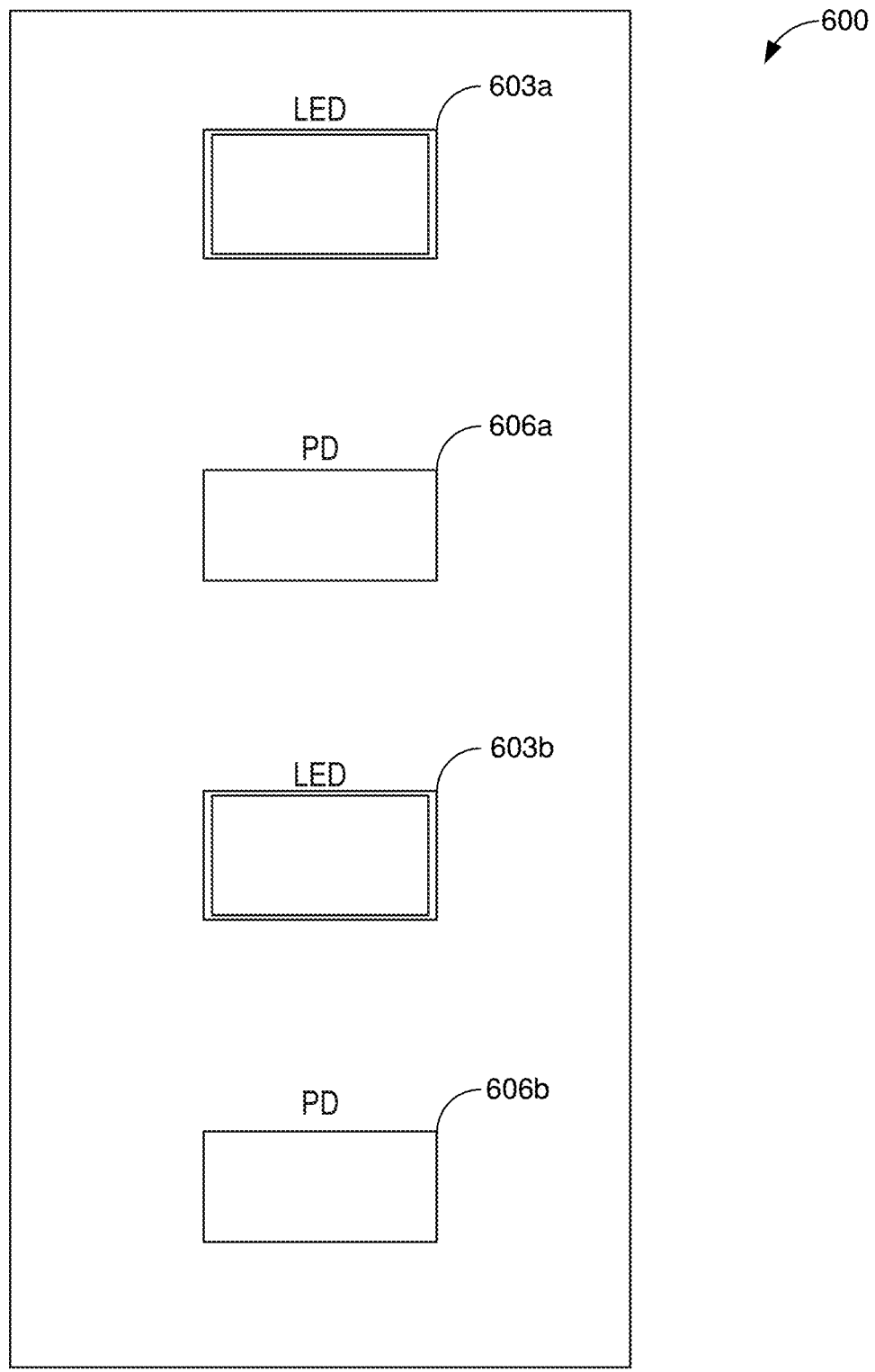
FIG. 6 illustrates a LED/PD array according to various embodiments of the present disclosure.

Turning to FIG. 6, shown is an LED/PD array 600 according to various embodiments of the present disclosure. The LED/PD array 600 can be an array board with one or more light emitting diodes (LEDs) 603*a* and 603*b* and one or more photodiodes (PDs) 606*a* and 606*b*. In some embodiments, more than one LEDs and more than one PDs can be alternated as shown (e.g., LED 603*a*, PD 606*a*, LED 603*b*, PD 606*b*, etc.). In multiple embodiments, the LED/PD array 600 may not have alternating LEDs and PDs. The LEDs 603*a*, 603*b* and PDs 606*a*, 606*b* can be spaced a predetermined distance 609. As an example, the LED 603*a* can be positioned the predetermined distance 609*a* from PD 606*a*, and the PD 606*a* can be positioned a predetermined distance 609*b* from the LED 603*b*, and the LED 603*b* can be positioned a predetermined distance 609*c* from PD 606*b*. In some embodiments, the predetermined distances 609*a-c* are the same distance. In other embodiments, the predetermined distances 609*a-c* may differ. In one embodiment, the predetermined distances 609*a-c* are between 6 mm and 12 mm (e.g., 6 mm, 9 mm, or 12 mm). In some embodiments, the LEDs 603*a*, 603*b* and PDs 606*a*, 606*b* can be pressed into the skin at a controlled distance of 0.5 mm to 1.5 mm.

In many embodiments, the LED/PD array 600 may include multiple rows and/or columns of LED/PD arrays. The multiple rows and/or columns of LED/PD arrays may include alternating LEDs and PDs, or may have two or more LEDs and proximate to each other and two or more PDs proximate to each other.

Figure 7:
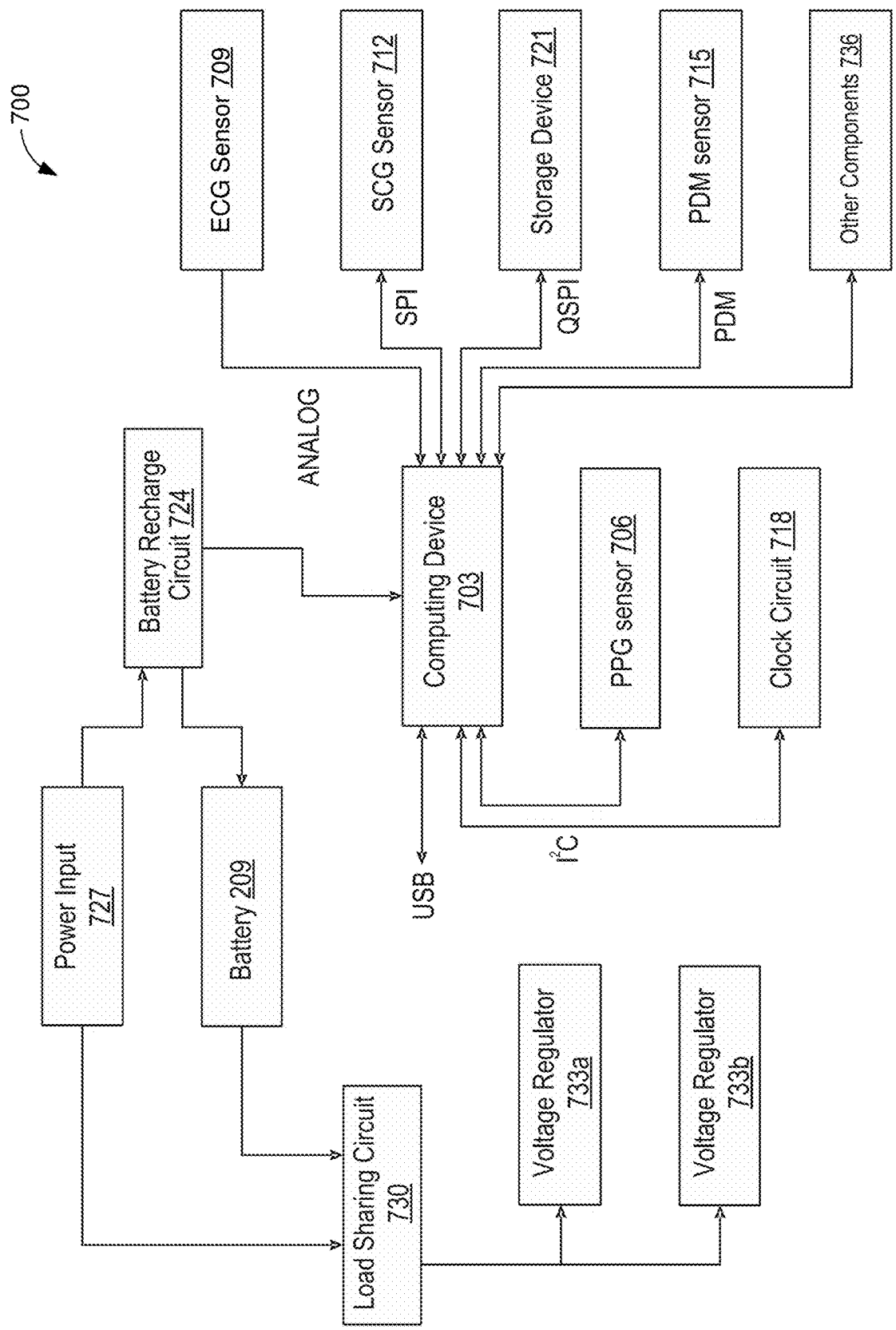
FIG. 7 illustrates a functional circuit diagram according to various embodiments of the present disclosure.

With reference to FIG. 7, shown is an example functional circuit diagram 700 for a patch device 103 (FIG. 1) according to various embodiments of the present disclosure. The circuit diagram 700 can include a computing device 703 in communication with one or more sensors 221 (FIG. 2) shown as PPG sensor 706, ECG sensor 709, SCG sensor 712, and PDM sensor 715 among other sensors. The computing device 703 can be in communication with a clock circuit 718, a storage device 721, and a battery recharge circuit 724.

In one embodiment, the PPG sensor 706 includes two PPG sensors and the SCG sensor 712 includes three SCG sensors. In at least one embodiment, specific components can be used, such as, e.g., the computing device 703 can be an nRF52 BLE module with an integrated antenna, the PPG sensor 706 can be an integrated circuit part number PPG MAX 30102, the ECG sensor 709 can be an integrated circuit part number ECG AD8232, and the SCG sensor 712 can be an integrated circuit part number SCG ADXL355. The PDM sensor 715 can include a microphone configured to monitor audio, such as, for example, audio generated by a chest of an individual. The PDM sensor 715 can be positioned to contact a skin of a patient. The PDM sensor 715 can be positioned proximate a lung or proximate heart of the individual. In one embodiment, the PDM sensor 715 is a pulse-density modulated microphone. In some embodiments, the ECG sensor 709 includes an ECG amplifier. The ECG sensor 709 (or other sensor 221) can include a heart rate sensor and a pulse oximeter.

The battery recharge circuit 724 can receive power from a power input 727 and use the received power to charge the battery 209. The power input 727 can be coupled to an external power signal and the battery recharge circuit 724 can store power from the external power signal in the battery 209. The load sharing circuit 730 can provide power from the battery 209 when the battery recharge circuit 724 is not receiving the external power signal and provide the input power signal from the power input 727 when the battery recharge circuit is receiving the external power signal. Stated differently, the load sharing circuit 730 can receive power from either the power input 727, the battery 209, or the power input 727 and the battery 209.

The load sharing circuit 730 can provide a power signal to one or more voltage regulators, such as voltage regulator 733a and 733b. In one embodiment, the voltage regulator 733a can provide a first input voltage to one or more circuit components and the voltage regulator 733b can provide a second input voltage to one or more other circuit components. The power/voltage regulator 733 can modify the input voltage from the load sharing circuit 730 to provide a specific voltage to other circuit components. In one embodiment, the power input 727, the battery recharge circuit 724, the battery 209, the load sharing circuit 730, and the one or more voltage regulators 733a and 733b form a power source circuit that provides a power signal to the PPG sensor 706, the ECG sensor 709, the SCG sensor 712, the PDM sensor 715, and the computing device 703, among other components in the circuit diagram 700.

In one embodiment, the load sharing circuit 730 receives an input voltage from the battery 209 of 3.7 volts (v) and an input voltage from the power input 727 of 5v. In one embodiment, the voltage regulator 733a generates a 3.3v signal and the voltage regulator 733b generates a 1.8v signal. Additional or fewer voltage regulators 733 can be used depending on voltage requirements of various circuit components in the circuit diagram 700.

The PPG sensor 706 can include an array board with one or more light emitting diodes (LEDs) and one or more photodiodes (PDs). In some embodiments, more than one LEDs and more than one PDs can be alternated on the board, such as, for example, LED. PD, LED, PD, LED, PD if three LEDs and three PDs were used. The LEDs and PDs can be spaced out along a line. In one embodiment, the space between each LED/PD and a next PD/LED between 6 mm and 12 mm (e.g., 6 mm, 9 mm, or 12 mm). The SCG sensor 712 can include one or more programmable digital filters.

The circuit diagram 700 can include other components 736, which may or may not be coupled directly to the computing device 703. The other components 736 can include one or more radio frequency filters coupled to the computing device 703 and one or more antennas coupled to the radio frequency filter. In one embodiment, the other components 736 include a gyroscope. In one embodiment, the other components 736 include an accelerometer. In one embodiment, the other components 736 include a compass. In one embodiment, the other components 736 include a digital motion processor. The digital motion processor can be configured to offload computation of motion processing algorithms from the computing device 703.

The computing device 703 can communicate with the PPG sensor 706, the SCG sensor, ECG sensor 709, the SCG sensor 712, the storage device 721, the PDM sensor 715, and other components 736 using I2C, SPI, QSPI, a GPIO line, or through another manner. The computing device 703 can receive a time from the clock circuit 718. The time may be received in the form of a timestamp (e.g., a number of seconds since a predetermined point in time, such as, for example, a number of seconds since Jan. 1, 1970 at 0:00:00 GMT) or the computing device 703 can convert the time from the clock circuit 718 into a timestamp. In some embodiments, the computing device 703 can capture a timestamp and associate the timestamp with each measurement taken from one of the sensors 221. The timestamps can be used to determine when each measurement was taken when analyzing the measurement data.

The computing device 703 can read sensor measurements from the PPG sensor 706, ECG sensor 709, SCG sensor 712, PDM sensor 715 and other sensors 221. In some embodiments, the computing device 703 can verify an integrity of the data being read. As an example, the computing device 703 can receive the sensor measurements in one or more data packets. The computing device 703 can verify an integrity of the data packets by verifying a CRC portion of the data packet, checking that an expected parity bit is set correctly, verifying a checksum portion of the data packet, verifying a digital signature of the data packet, verifying that each data component is within a valid data range, or by performing other validity checks. The computing device 703 can store the measurements on the storage device 721. The stored measurements can be transmitted via a wired (e.g., via a data port such as USB, JST, or network port) or wireless transmission (e.g., Wi-Fi, Bluetooth, Zigby, Z-Wave, NFC, LoRaWAN, or other wireless transmission) to an external device or service.

The computing device 703 can compute one or more data values based on the sensor measurements from sensors 221. As an example, the computing device 703 can compute a respiratory-induced amplitude variation, and a respiratory-induced intensity variation, a respiratory-induced frequency using PPG sensor measurements. In some embodiments, the computing device 706 can compute, calculate, and determine cardiorespiratory parameters such as heart rate, heart rate variability, pre-ejection period, aortic valve opening magnitude, left ventricular ejection time, tidal movements, Actigraphy, SCG fiducial timing, SCG fiducial amplitude, and other data values using measurements from sensors 221.

In multiple embodiments, the computing device 706 may compute, calculate, and determine the cardiorespiratory parameters by measuring the seismocardiogram via the chest accelerometer and the electrocardiogram via the ECG sensor (e.g., two electrode ECG sensor) on the patch device. In one embodiment, the computing device 706 may synchronously measure the seismocardiogram via the chest accelerometer and the electrocardiogram via the ECG sensor (e.g., two electrode ECG sensor) on the patch device to determine the cardiorespiratory parameters. In many embodiments, the computing device 706 can compute, calculate, and determine disordered breathing parameters, such as obstructive sleep apnea, central sleep apnea, Cheyne-Stokes breathing, and/or chronic obstructive pulmonary disease. The computing device 706 may compute, calculate, and determine the disordered breathing parameters by measuring the seismocardiogram and the respiratory tidal motions via the chest accelerometer, and oxygen desaturation levels via the PPG sensor. In one embodiment, the computing device 706 may synchronously measure the seismocardiogram and the respiratory tidal motions via the chest accelerometer, and oxygen desaturation levels via the PPG sensor to determine the disordered breathing parameters.

Figure 8:
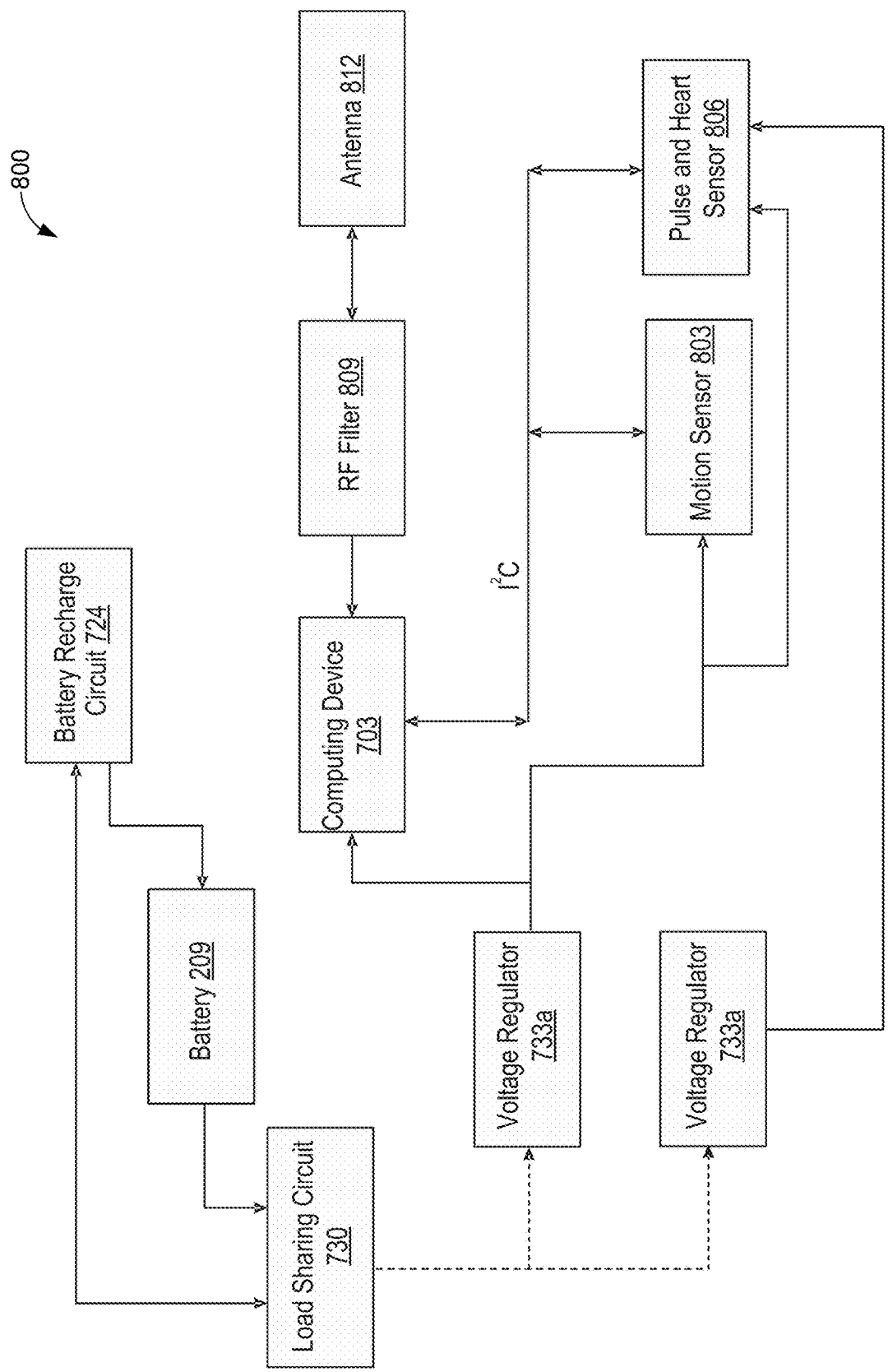
FIG. 8 illustrates a functional circuit diagram according to various embodiments of the present disclosure.

With reference to FIG. 8, shown is an example functional circuit diagram 800 for a patch device 103 (FIG. 1) according to various embodiments of the present disclosure. It can be appreciated that embodiments of the present disclosure can use various components and/or portions from the circuit diagrams 700 and 800, which can be combined, interchanged, replaced, or used in various variations. The circuit diagram 800 can include a computing device 703 in communication with one or more sensors 221 (FIG. 2) shown as a motion sensor 803 and a pulse and heart sensor 806 among other sensors. The computing device 703 can communicate with an RF filter 809 and an antenna 812. Similar to circuit diagram 700, the circuit diagram 800 can also include a battery recharge circuit 724, one or more batteries 209, a load sharing circuit 730, one or more voltage regulators 733a and 733b, and potentially other components.

In one embodiment, the motion sensor 803 can include a 9-axis motion tracking sensor including a 3-axis gyroscope, a 3-axis accelerometer, a 3-axis compass, and a digital motion processor. In one embodiment, the motion sensor 803 corresponds to part number ICM-20948. The pulse and heart sensor 806 can include a pulse oximeter. The pulse and heart sensor 806 can include a heart rate sensor and other components. In one embodiment, the pulse and heart sensor 806 can be part number MAX30102 from Maxim Integrated.

Patches 900a and 900b are shown in FIGS. 9A and 9B, respectively. Patch 900a is a patch with a "standard" or initial air gap 918. Modified patch 900b is a patch with a modified or reduced air gap 924.

FIGS. 9A and 9B each show the skin of a patient 912 in contact with a patch 900 (e.g., 900a and 900b) via a PPG sensor 909 (e.g., 909a and 909b, which, in some embodiments, is surrounded by a foam layer) connected to or passed through an adhesive layer 906 (e.g., 906a and 906b). In the embodiments shown in FIGS. 9A and 9B, the adhesive layer 906 is connected a board 903 (e.g., a circuit board or other rigid components of the patch disclosed herein). In various embodiments, the patch 900 creates a gap of approximately 1.3 mm between the board 903 and the skin of the patient 912.

Patch 900a shown in FIG. 9A includes an air gap 918 of approximately 1.1 mm between the skin of the patient 912 and a lower surface of the adhesive layer 906a. In various embodiments, the adhesive layer 906a includes a thickness 915 of approximately 0.2 mm. The air gap 918 (approximately 1.1 mm) and the thickness 915 of the adhesive layer 906a (approximately 0.2 mm) create a gap of approximately 1.3 mm between the board 903 and the skin of the patient 912.

Modified patch 900b shown in FIG. 9B includes an air gap 924 of approximately 0.7 mm between the skin of the patient 912 and a lower surface of the adhesive layer 906b. The adhesive layer 906b includes a thickness 921 of approximately 0.6 mm. The air gap 924 (approximately 0.7 mm) and the thickness 921 of the adhesive layer 906b (approximately 0.6 mm) create a gap of approximately 1.3 mm between the board 903 and the skin of the patient 912.

Figure 10A:
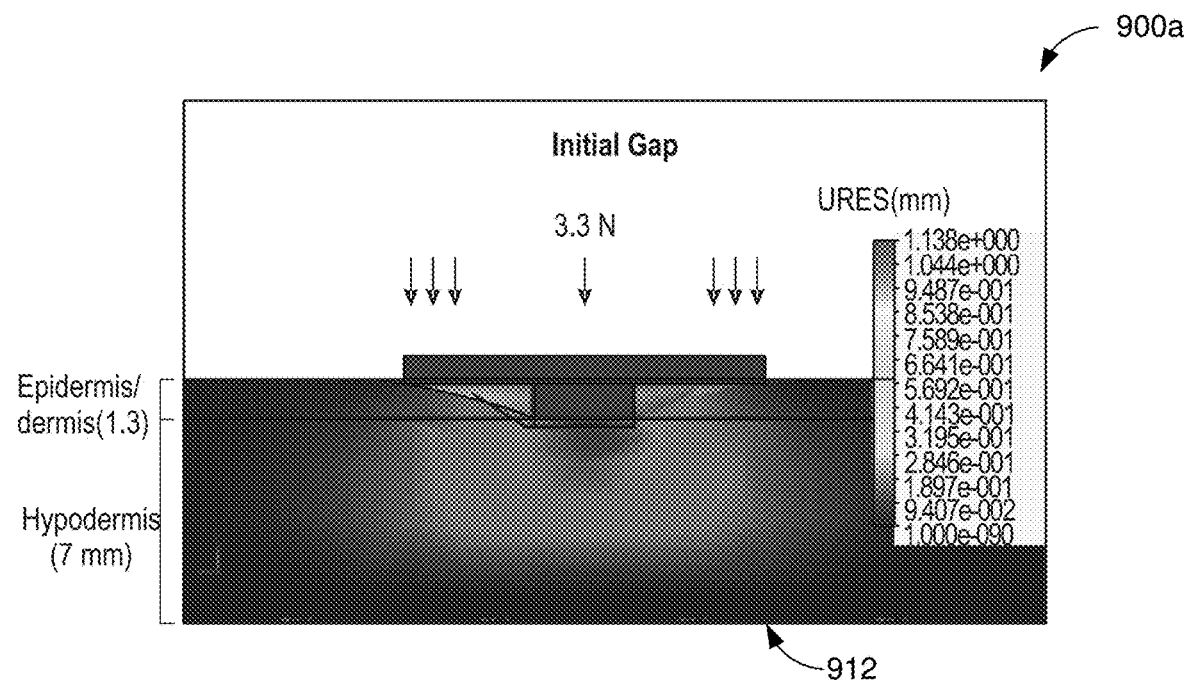
FIGS. 10A and 10B illustrate analyses of patch devices according to various embodiments of the present disclosure.
Figure 10B:
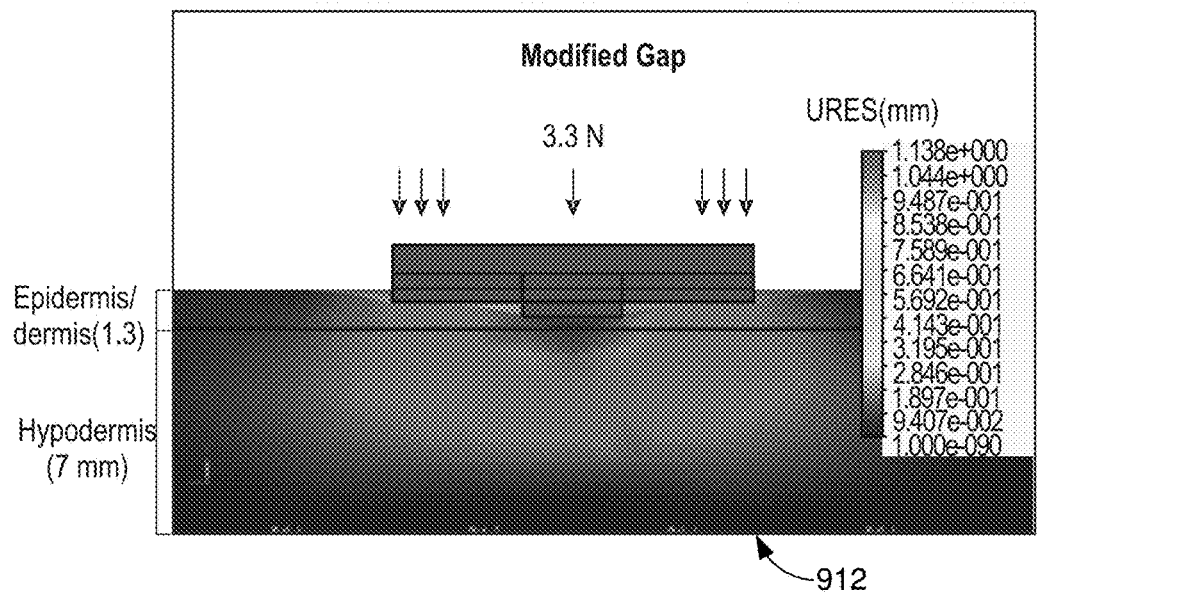

Turning now to FIGS. 10A and 10B, these figures show a finite element analysis of patches 900a and 900b, according to one embodiment of the present disclosure, with a unit of deflection (URES) in millimeters scale on the right of each figure. As shown in FIGS. 10A and 10B, patch 900a and modified patch 900b are under a uniform compression force (approximately 3.3 N). In the embodiments shown, modified patch 900b does not penetrate as far into the skin of the patient 912 and has a more distributed pressure profile (likely resulting in more comfort for the patient and more consistent sensor readings).

Figure 11A:
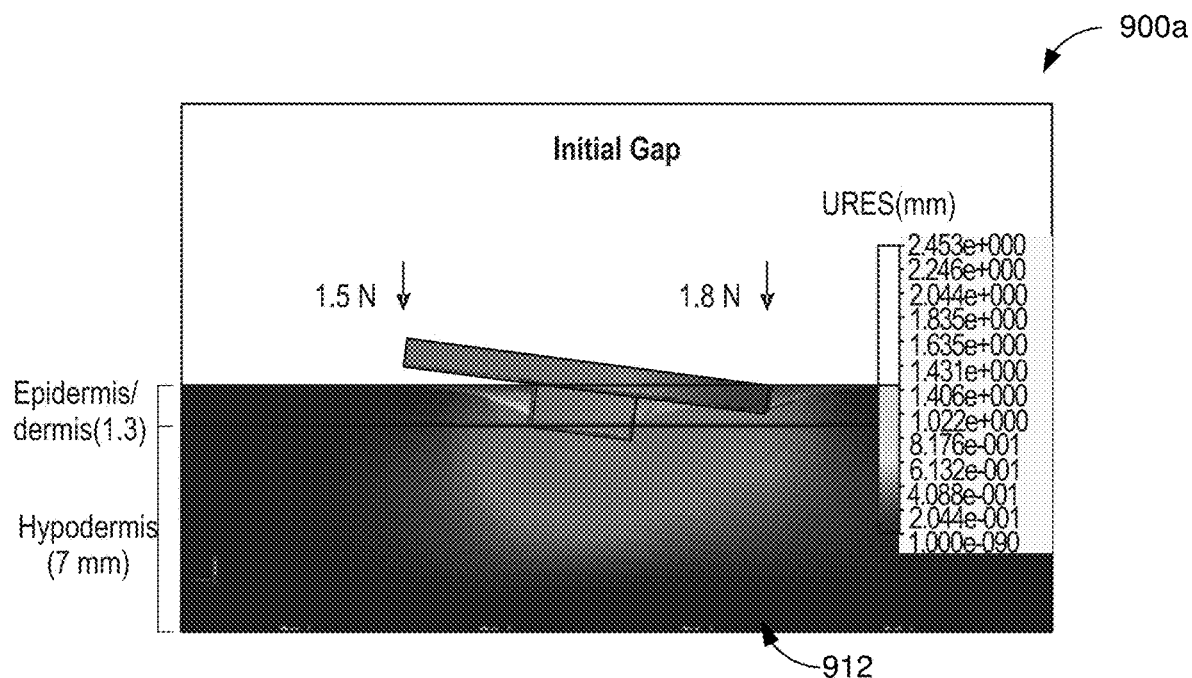
FIGS. 11A and 11B illustrate analyses of patch devices according to various embodiments of the present disclosure.
Figure 11B:
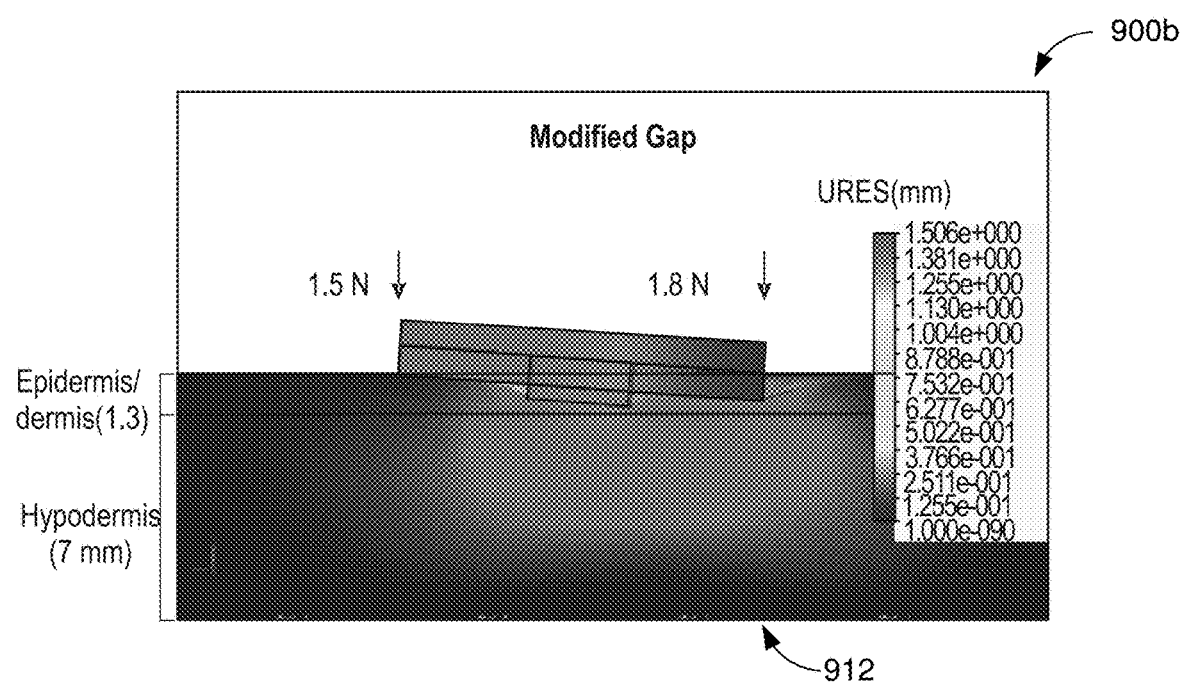

FIGS. 11A and 11B show a finite element analysis of patches 900a and 900b, according to one embodiment of the present disclosure, with a unit of deflection (URES) in millimeters scale on the right of each figure. As shown in FIGS. 11A and 11B, patch 900a and modified patch 900b are under a compressive force of about 1.8 N on a right side of each patch and a compressive force of about 1.5 N on a left side of each patch (e.g., patches 900a and 900b are modeled under an unbalanced compressive force). In the embodiments shown in FIGS. 11A and 11B, modified patch 900b does not penetrate as far into the skin of the patient 912 and shows less rotation than patch 900a, thereby resulting in more consistent sensor readings. The modified patch 900b can include a greater overall quality of signal in comparison to the patch 900a when forces are applied to the patch.

The description above in relation to FIGS. 9A-11B includes certain dimensions. As will be understood from discussions herein, these dimensions (and others discussed herein) are approximate and one of ordinary skill in the art would understand that additional dimensions are contemplated. For example, the gap (including the air gap 918 or air gap 924) may be any suitable distance, including, but not limited to 1.0, 1.1, mm, 2.0, 2.1, 2.2, 2.3 mm, 0.1-0.5 mm, 10.0 mm, etc. In some embodiments, the adhesive layer 906 (e.g., 906a and 906b) may include a thickness (e.g., 915 or 921) of about 0.1-10 mm, 0.2 mm, 1.0 mm, 1.5 mm, 2.0 mm, 2.1 mm, 2.2 mm, 5.0 mm, 10.0 mm, etc., and may include more than one adhesive layer. In at least one embodiment, the air gap 918 or air gap 924 may be any suitable dimension, including, but not limited to 1 mm, 2 mm, 0.1-0.5 mm, 10.0 mm, etc.

As discussed herein, in at least one embodiment, a patch includes a PPG sensor (e.g., PPG sensor 221), which may include a plurality of light emitting diodes (LEDs) and a plurality of photodiodes (PDs). In this embodiment (and others), the PPG sensor is attached to a patient via a flexible and stretchable (e.g., conformal) patch. As also discussed herein, a conformal patch provides improved signal quality and consistency over rigid patch designs or other types of sensors.

FIGS. 12A-12D show an exemplary patch 1200a in accordance with various embodiments discussed herein and rigid patch 1200b. Each of FIGS. 12A-12D include an exemplary PPG reading/signal 1203 (1203a-1203d), where the box shown at 1203 represents the PPG reading signal when the patch shown is stretched (FIGS. 12A and 12C) or pivoted/rotated (FIGS. 12B and 12D).

As shown in FIGS. 12A and 12B, patch 1200a includes a flexible circuit 1206a (e.g., material layer 222), an adhesive layer 1209, and a PPG sensor 221 in contact with a skin of a patient 912. As will be understood from discussions herein, the exemplary patch 1200a may include other components discussed in the present disclosure. Further, as discussed above in relation to FIGS. 9A-11B, the exemplary patch 1200a may include a minimized air gap to limit stress concentrations and signal variations, among other benefits.

FIG. 12A shows exemplary patch 1200a in a stretched position (e.g., stretched with the skin of a patient due to, for example, patient movement or breathing). FIG. 12A also shows an exemplary corresponding PPG reading/signal 1203a. As shown in FIG. 12A, there is little variation in the PPG signal due to stretching of the patch 1200a (e.g., the signal within the box shown in FIG. 12A is substantially similar to the signal outside of the box).

FIG. 12B shows exemplary patch 1200a and corresponding PPG reading/signal 1203b when the patch 1200a pivots/is rotated. As shown in FIG. 12B, the PPG reading/signal varies little when the patch 1200a pivots/is rotated (there is a slight spike, but overall the reading/signal overall stays relatively constant).

FIGS. 12C and 12D show a rigid patch 1200b, which includes a rigid circuit PCB 1206b operatively connected to a PPG sensor 221 contacting a patient's skin 912. In FIG. 12C, the rigid patch 1200b is stretched (or the patient's skin is stretched), resulting in a corresponding change in PPG reading/signal shown at 1203c (e.g., the signal within the box is substantially changed from the signal shown outside the box). In FIG. 12D, the rigid patch 1200b is pivoted/rotated, resulting in corresponding change in PPG reading/signal shown at 1203d (e.g., (e.g., the signal within the box is substantially changed from the signal shown outside the box).

As demonstrated in the above FIGS. 9-12, the conformal patch discussed herein results in at least improved PPG signal amplitude and increased signal consistency (e.g., less variations from outside factors). The below Table 1 demonstrates the results of four tests comparing a rigid patch and a conformal/flexible patch as discussed herein. In the below Table 1, "Amp." is "Amplitude," "Score Red" is a confidence score for a red sensor, and "Score IR" is a confidence score for an infrared (IR) sensor.

TABLE 1

COMPARISON OF RIGID PPG SENSOR ENCLOSURE AND CONFORMAL PATCH

| Subject | Type | Amp. Red | Change | Amp. IR | Change | Score Red | Change | Score IR | Change |
|---|---|---|---|---|---|---|---|---|---|
| 1 | Rigid | 124.79 | 52.0% | 348.72 | 34.5% | 0.97 | -4.4% | 0.98 | 0.0% |
|   | Flex | 189.66 |  | 468.95 |  | 0.93 |  | 0.98 |  |
| 2 | Rigid | 64.43 | 217.2% | 166.68 | 68.3% | 0.57 | 37.6% | 0.86 | 8.1% |
|   | Flex | 204.40 |  | 280.58 |  | 0.79 |  | 0.93 |  |
| 3 | Rigid | 143.24 | 115.3% | 254.71 | 102.1% | 0.86 | 6.8% | 0.87 | 9.0% |
|   | Flex | 308.42 |  | 514.66 |  | 0.92 |  | 0.95 |  |
| 4 | Rigid | 143.24 | 115.3% | 254.71 | 102.1% | 0.46 | 5.0% | 0.70 | 7.0% |
|   | Flex | 308.42 |  | 514.66 |  | 0.48 |  | 0.75 |  |
| Average Change | Flex/Rigid | 125.0% |  | 76.7% |  | 11.2% |  | 6.0% |  |

As shown in Table 1, on average, red amplitude increased 125.0% for a flexible patch (e.g., a conformal patch as discussed herein in various embodiments), infrared amplitude increased 76.7%, confidence in the red amplitude increased by 11.2%, and confidence in the infrared score increased 6.0%. These results represent an approximately two-times improvement in signal amplitude using a conformal/flexible patch compared to a rigid design.

With reference to FIG. 13, shown is an exemplary reflective PPG device 1300 that can be operatively connected to the disclosed patch device (e.g., patch device 103 in FIG. 1) according to various embodiments of the present disclosure. In some embodiments, the reflective PPG device 1300 can be a sensor 221. The patch device may utilize reflective PPG device 1300 to optically measure the pulsatile arterial volume (e.g., volumetric blood flow). The reflective PPG device 1300 may measure the volumetric blood flow by emitting a light ray from a light source 1303 (e.g., LEDs). The light ray can reflect off of the blood flow. A photo detector (e.g., PDs) can detect the reflected light ray. The reflective PPG device 1300 may be attached to a user at the user's chest.

The PPG device 1300 can include two or more LED types. In some embodiments, the PPG device 1300 can sense two different depths tissue of the patient. In one embodiment, a first type of LED can be used to sense a first depth while a second type of LED can be used to sense a second depth. The first depth can correspond to superficial tissue and the second depth can correspond to deeper vessel tissue. In some embodiments, a PPG sensor 221 including PPG device 1300 can sense both depths simultaneously.

With reference to FIG. 14, shown are exemplary chest acceleration graphs 1400 that the disclosed patch device 103 (FIG. 1) can produce (e.g. provide data to a testing service 233 for production by a display of a user's computer or produce by the patch device 103 on an attached display) according to various embodiments of the present disclosure. The exemplary chest acceleration graphs 1400 may include an ECG graph, a seismocardiography (SCG) graph, a gyrocardiography (GCG) graph and/or potentially other health parameter and sensor graphs. The sensors 221 (e.g., an accelerometer, ECG sensor, gyroscope) can take ECG, SCG, and GCG measurements and the system may produce the chest acceleration graphs 1400 from these ECG, SCG, and GCG measurements. The SCG graph may show chest acceleration that is associated with sleep apnea. The GCG graph may show heart motions captured via a sensor 221 using angular motion. The ECG graph may show electrical signals from the user's heart over time.

The system may derive chest acceleration metrics from measurements taken by the sensors 221 (e.g., accelerometer, gyroscope, ECG sensor, etc.). The chest acceleration metrics may include, but are not limited to, tidal movements, actigraphy, SCG fiducial timing, and SCG fiducial amplitude. The tidal movements metric may be the measure of volume changes of thoracic cavity, and may be an alternative method for measuring respiratory effort. The actigraphy metric may be the measure of movements during sleep, and may be an alternative method for measuring sleep staging. The SCG fiducial timing metric may be the measure of sympathetic activity and respiratory function, and may be an alternative or additional method for measuring respiration and peripheral arterial signal (PAT). The SCG fiducial amplitude metric may also measure the sympathetic activity and respiratory function, and may also be an alternative or additional method for measuring respiration and (PAT). In some embodiments, two or more methods can be used to measure and verify health parameters, such as respiration and (PAT) among others disclosed herein.

The redundant measurements can be used to determine when a particular sensor 221 is positioned improperly or is experiencing inaccurate measurements.

Also shown in FIG. 14 is an exemplary user 1403 with a disclosed patch device attached to the user's chest, according to one embodiment of the present disclosure. The disclosed patch device may be attached to the user's chest as described herein. The accelerometer and gyroscope may monitor the position and chest motion of the user when attached to the chest of the user.

Figure 15:
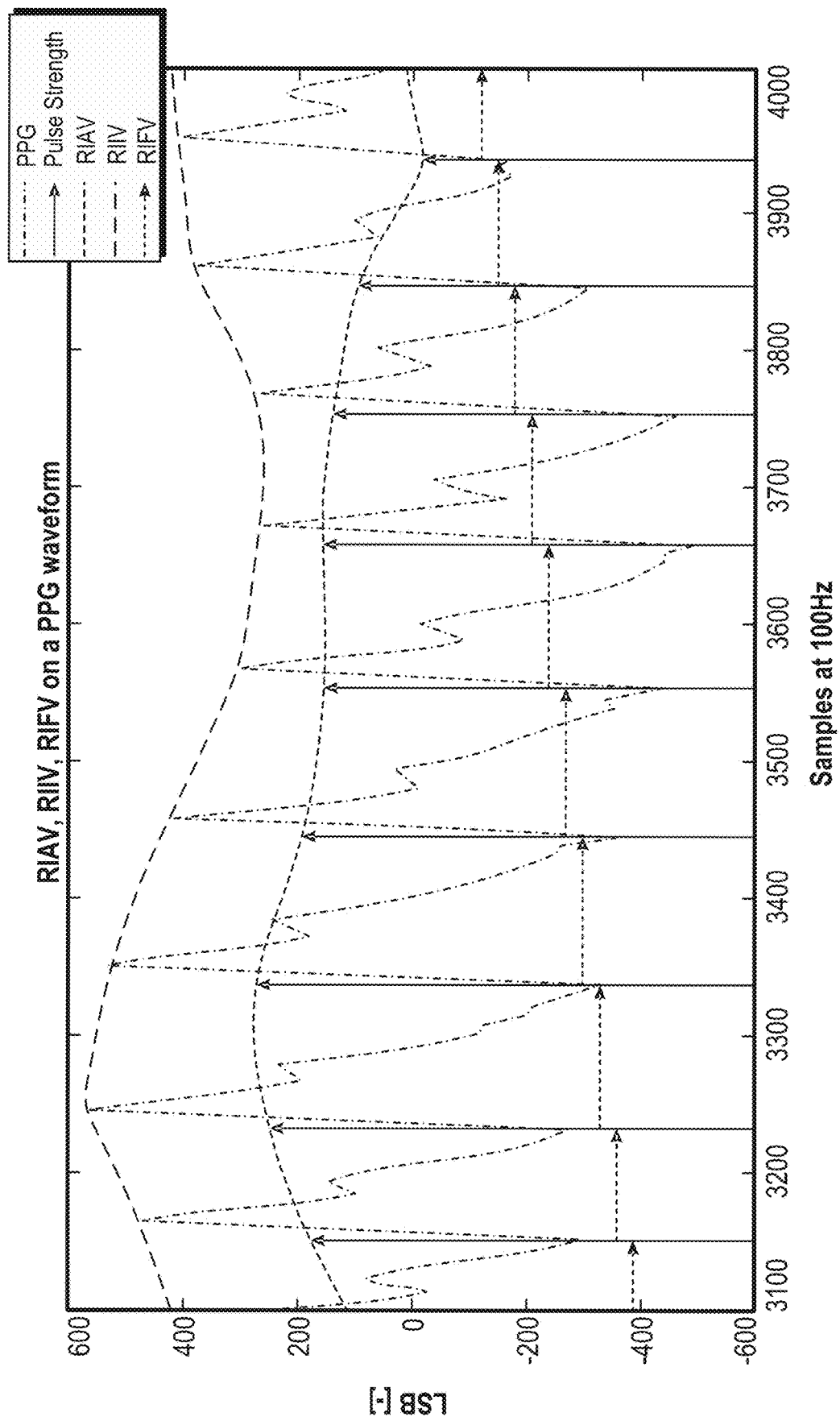
FIG. 15 is a chart of sensor measurements from a PPG sensor of a patch device according to various embodiments of the present disclosure.

With reference to FIG. 15, shown is an exemplary PPG waveform graph 1500 that the disclosed patch device can produce, according to various embodiments of the present disclosure. The patch device may utilize PPG sensors to produce the PPG waveform graph 1500. The PPG waveform graph 1500 may be utilized in detecting sleep apnea, disordered breathing, and related cardiorespiratory parameters. According to one embodiment, the PPG waveform graph 1500 shows sample measurements of PPG respiratory analysis for respiratory-induced intensity variation (RIIV), a respiratory-induced amplitude variation (RIAV), and respiratory-induced frequency variation (RIFV). RIIV can be a measurement of a variation in perfusion baseline due to changes in intrathoracic pressure. RIAV can be a measurement of a variation in peripheral pulse strength. RIFV can be a measurement of the variation of heart rate frequency during respiration.

The PPG waveform graph 1500 may show PPG measurements taken from the PPG sensor(s). The PPG waveform graph 1500 can show the RIIV, RIAV, and RIFV that are based on the PPG measurements. The PPG waveform graph 1500 has an x-axis and a y-axis. The x-axis of the PPG waveform graph 1500 can show PPG measurement samples at 100 Hz taken over a period of time. The y-axis of the PPG waveform graph 1500 can show the lower side band (LSB) amplitude of the PPG measurement samples.

Figure 16A:
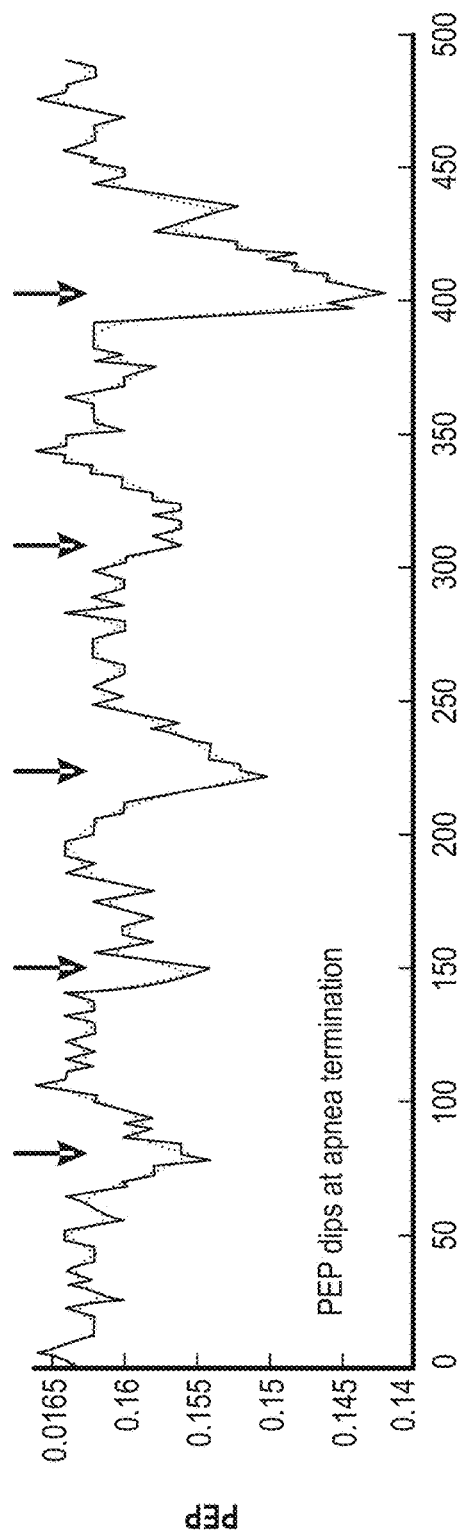
FIGS. 16A and 16B are charts of sensor measurements from a patch device according to various embodiments of the present disclosure.

With reference to FIG. 16A, shown is an exemplary pre-ejection period (PEP) graph 1600A that the disclosed patch device 103 (FIG. 1) can produce, according to various embodiments of the present disclosure. The PEP graph 1600A can show the points at which an apnea event terminates for a user with obstructive sleep apnea (OSA).

A user with OSA may be subject to a series of respiratory disturbances (e.g., disordered breathing or apnea events) that the patch device can measure via the sensors 221 (e.g., an accelerometer). A user with OSA may have restricted breathing during the series of respiratory disturbances, which can lead to a decrease of blood-oxygen levels. The decrease of blood-oxygen levels can trigger a sympathetic arousal, which can be characterized by an increase in heart rate (tachycardia) and respiration rate (tachypnea). The increase in heart rate can cause an increase in cardiac inotropy, which can shorten the pre-ejection period (PEP).

The PEP graph 1600A can show PEP measurements over time. In the PEP graph 1600A, the PEP measurements dip at apnea termination (e.g., at the end of the respiratory disturbance), as shown by the arrows.

Figure 16B:
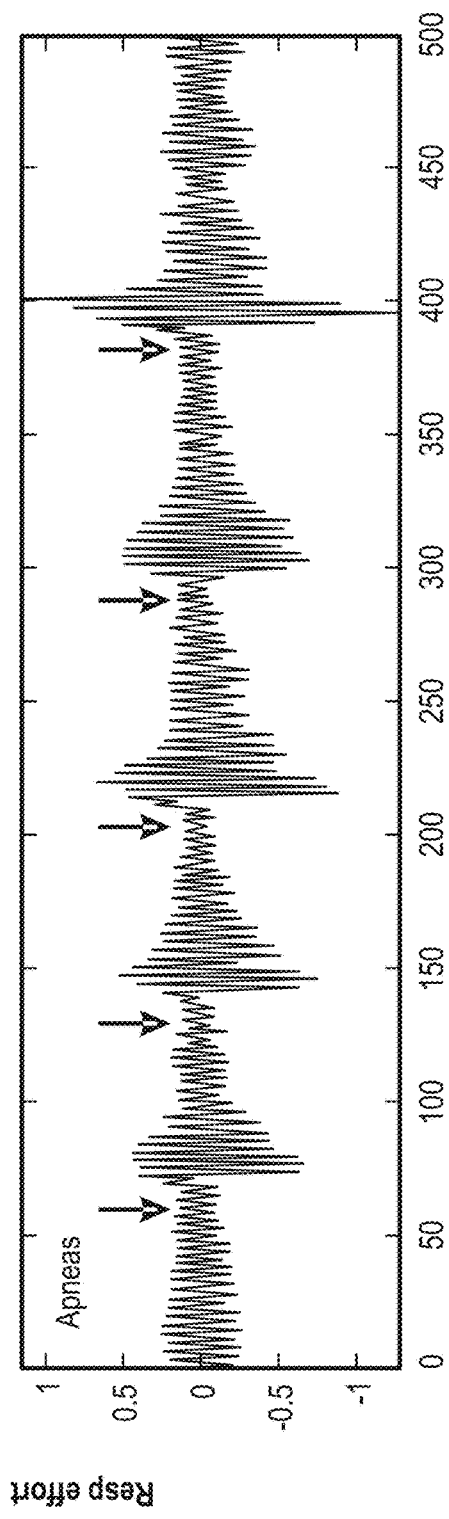

With reference to FIG. 16B, shown is an exemplary respiratory effort graph 1600B that the disclosed patch device 103 (FIG. 1) can produce, according to various embodiments of the present disclosure. The respiratory effort graph 1600B can show the respiratory effort for a user over time. The respiratory effort for a user with OSA can decrease if a respiratory disturbance (e.g., disordered breathing occurs), such as an airway obstruction. The disclosed patch device may detect the reduction in respiratory effort via the sensors 221 (e.g., an accelerometer). Once the respiratory disturbance is terminated, the respiratory effort of the user increases. For example, from time 150 to 200 on respiratory effort graph 1600B, the respiratory effort amplitude is decreasing, indicating a respiratory disturbance. At about time 210, the respiratory effort amplitude increases, indicating that the respiratory disturbance is terminated.

Figure 17A:
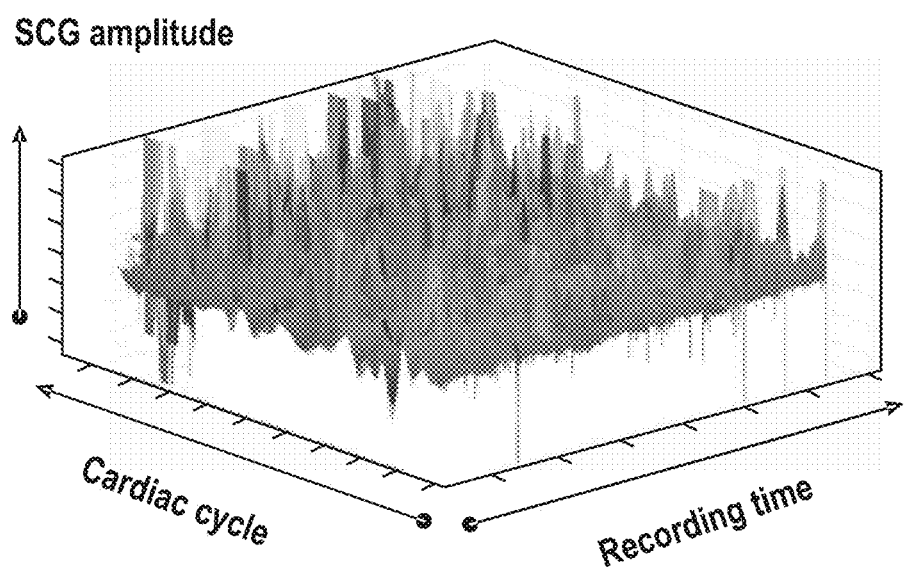
FIG. 17A is a waterfall view of a plot of sensor measurements from an SCG sensor of a patch device according to various embodiments of the present disclosure.

With reference to FIG. 17A, shown is an exemplary waterfall plot of average SCGs 1700A that the disclosed patch device can produce, according to various embodiments of the present disclosure. The SCG sensor 221 (FIG. 2) can measure the changes in thoracic or pleural pressures (cardiopulmonary interaction) and the data may show amplitude modulation. The waterfall plot of average SCGs 1700A is a three-dimensional graph that may show the SCG amplitude (y-axis) during a cardiac cycle (x-axis) over a period of time (z-axis).

Figure 17B:
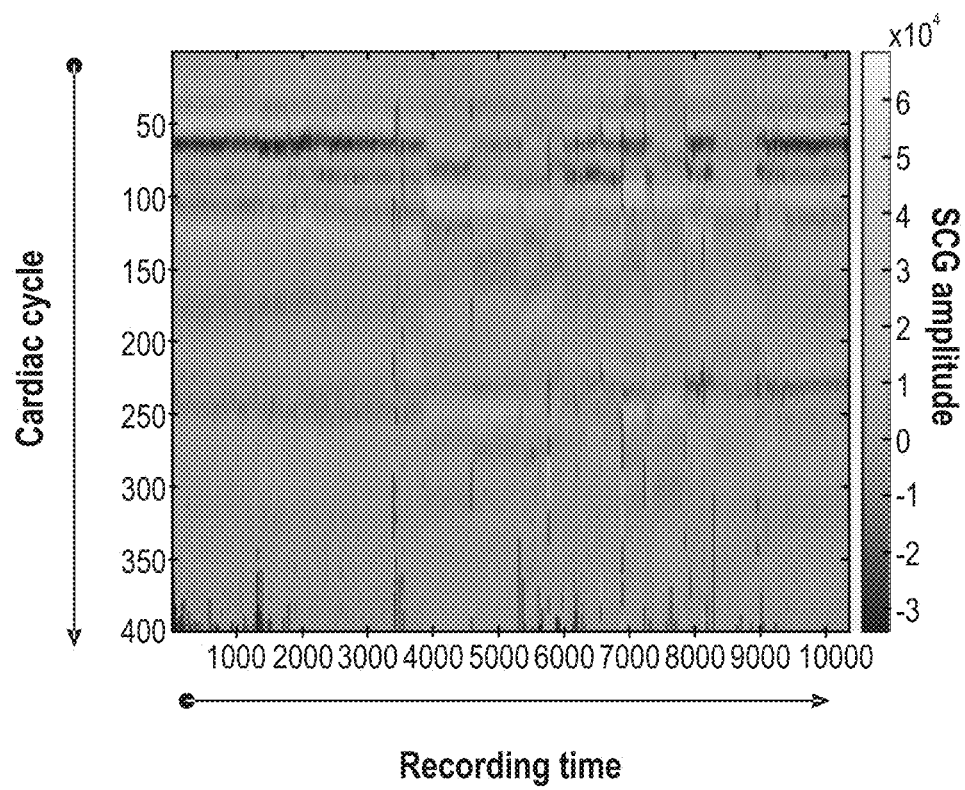
FIG. 17B is a top view of a plot of sensor measurements from an SCG sensor of a patch device according to various embodiments of the present disclosure.

With reference to FIG. 17B, shown is a top view 1700B of the exemplary waterfall plot of average SCGs 1700A that the disclosed patch device 103 (FIG. 1) can produce, according to various embodiments of the present disclosure. The top view of the exemplary waterfall plot of average SCGs 1700A distinguishes the SCG amplitude by color, allowing the exemplary waterfall plot of average SCGs 1700A to be shown as a two-dimensional chart.

Figure 17C:
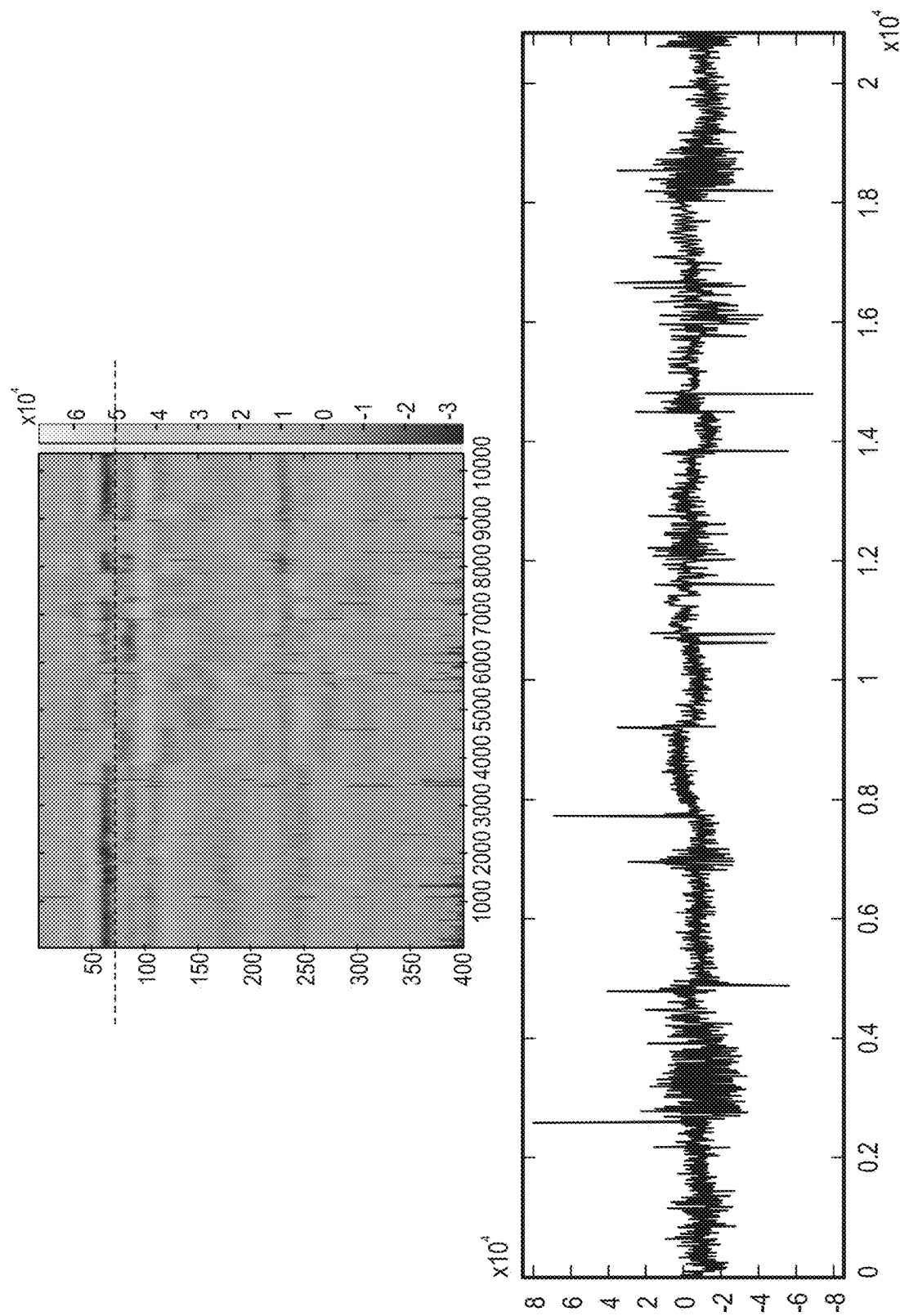
FIG. 17C is a cross-sectional view of a plot of sensor measurements from an SCG sensor of a patch device according to various embodiments of the present disclosure.

With reference to FIG. 17C, shown is an exemplary SCG amplitude chart 1700C for a certain cardiac cycle sample from the waterfall plot of average SCGs 1700A that the disclosed patch device 103 (FIG. 1) can produce, according to various embodiments of the present disclosure. The SCG amplitude chart 1700C can be a slice of the waterfall plot of average SCGs 1700A that can show the SCG amplitude of a user at a certain cardiac cycle (y-axis) over a period of time (x-axis). For example, at time 0.6, the SCG amplitude is around 0, and at time 0.4, the SCG amplitude may be around −2.

Figure 18:
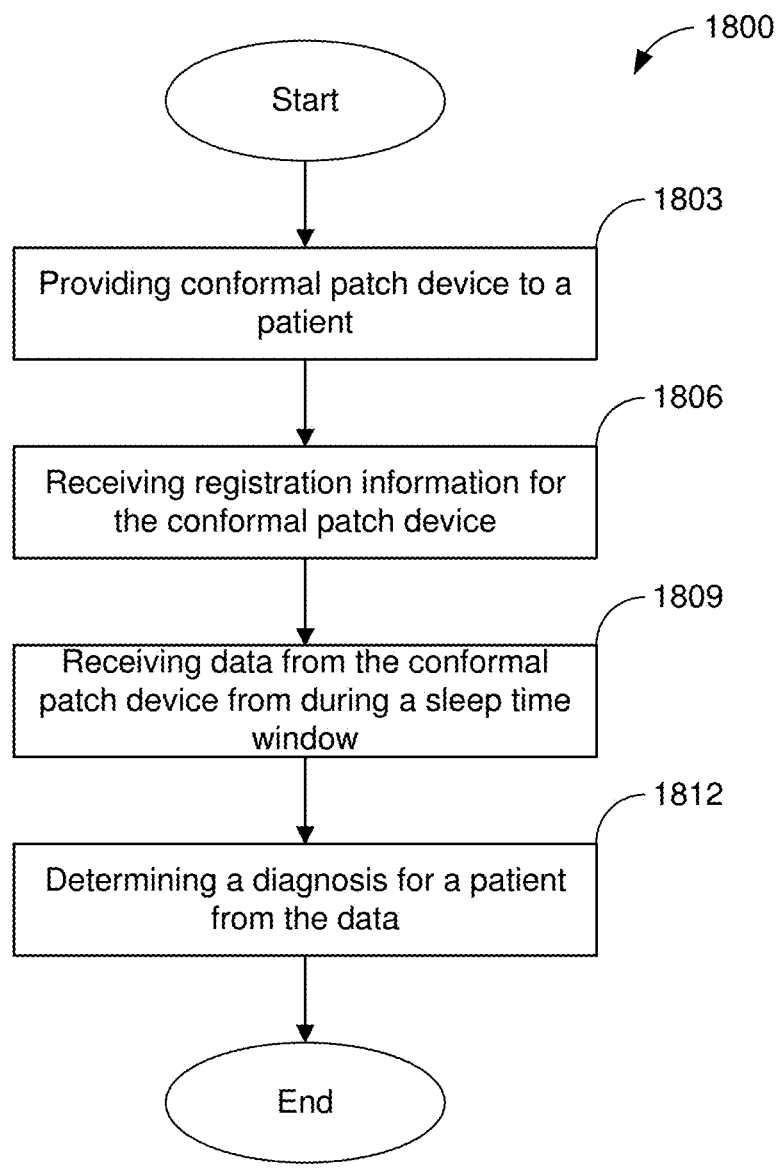
FIGS. 18 and 19 are flowcharts illustrating one example of functionality implemented as portions of the patch device and computing environment in the sensing environment of FIG. 2 according to various embodiments of the present disclosure.

Turning to FIG. 18, shown is a flow chart of a process 1800 according to various embodiments of the present disclosure. In some embodiments, portions of the process 1800 can be performed in a computing environment 203

(FIG. 2). In some embodiments, one or more of the features described for process 1800 can be performed by the patch application 218 without involving or in coordination with the testing service 233.

At box 1803, the process 1800 includes providing a conformal patch device to a patient. For example, the patch device 103 (FIG. 1) can be provided to a patient (e.g., mailed, shipped, provided via a doctor's office, etc.). In some embodiments, the testing service 233 can receive an order for one or more patch device 103. The testing service 233 can identify one or more available patch device 103. The testing service 233 can initiate shipping of the identified available patch devices 103 to one or more shipping address for a user or physician.

In some embodiments, when a test is completed or a patch device 103 is no longer needed, the testing service 233 can, but is not limited to, 1) initiate return shipping of the patch device, transfer data from the patch device 103, wipe the data actively from the storage device (e.g., flash memory) of the patch device. The data wipe can include actively writing new data to previously used memory locations on the storage device to permanently erase the patient data and ensure future user cannot extract confidential data.

At box 1806, the process 1800 includes receiving registration information for the conformal patch device. For example, the testing service 233 can receive registration information for the patch device 103. Once received, a user may input a serial number, capture a QR code, or enter other information to a web interface (or other user interface) to register the patch device 103. The testing service 233 may provide an authenticated user experience allowing a patient to enter patient information and pair or register patch devices 103 for use by the patient. In some embodiments, the use of a patch device 103 is temporary (e.g., to perform a particular series of tests), and the testing service 233 may associate test data 245 received from a patch device 103 registered with the patient (e.g., via user data 242) until the patch device 103 is received back for processing and redeployment. Once received back, the testing service 233 can disassociate the patch device 103 from the user account for future test data 245.

At box 1809, the process 1800 includes receiving data from the conformal patch device from during a sleep time window. As an example, the testing service 233 can communicate with one or more patch devices 103 to transfer sensor data 224 and result data 227 from one or more patient tests. The term "sleep time window" or similar term as used herein can include any period of time that a test is performed including when a patient is awake. A test may be started and stopped where the sleep time window begins at the start and ends at the stop. In some embodiments, the period of time may run continuously (e.g., the patch device 103 can be worn continuously through day and night cycles over multiple hours, days, weeks, etc. to collect data). The term "sleep" is not intended to be limiting to while a patient is sleeping. The patient tests can correspond to sleep windows (or intended sleep windows even if a patient fails to sleep for some or all of the time window). The testing service 233 can store the sensor data 224 and the result data 227 in test data 245 associated with a user account in user data 242. The user account associated to the data can automatically be selected based on a user account that registered the device at box 1806. The testing service 233 can collect testing data from multiple users and collect multiple tests for each user.

At box 1812, the process 1800 includes determining a diagnosis for a patient from the received data. For example, the testing service 233 can process the collected testing data from test data 245. The testing service 233 can analyze the test data 245 to identify one or more diagnosis for the patient. In some examples, the diagnosis is that the patient is healthy and no problems were identified in the test data 245. In other examples, the testing service 233 can determine sleep apnea, disordered breathing, and/or related cardiorespiratory parameters that may occur during a testing time window.

Figure 19:
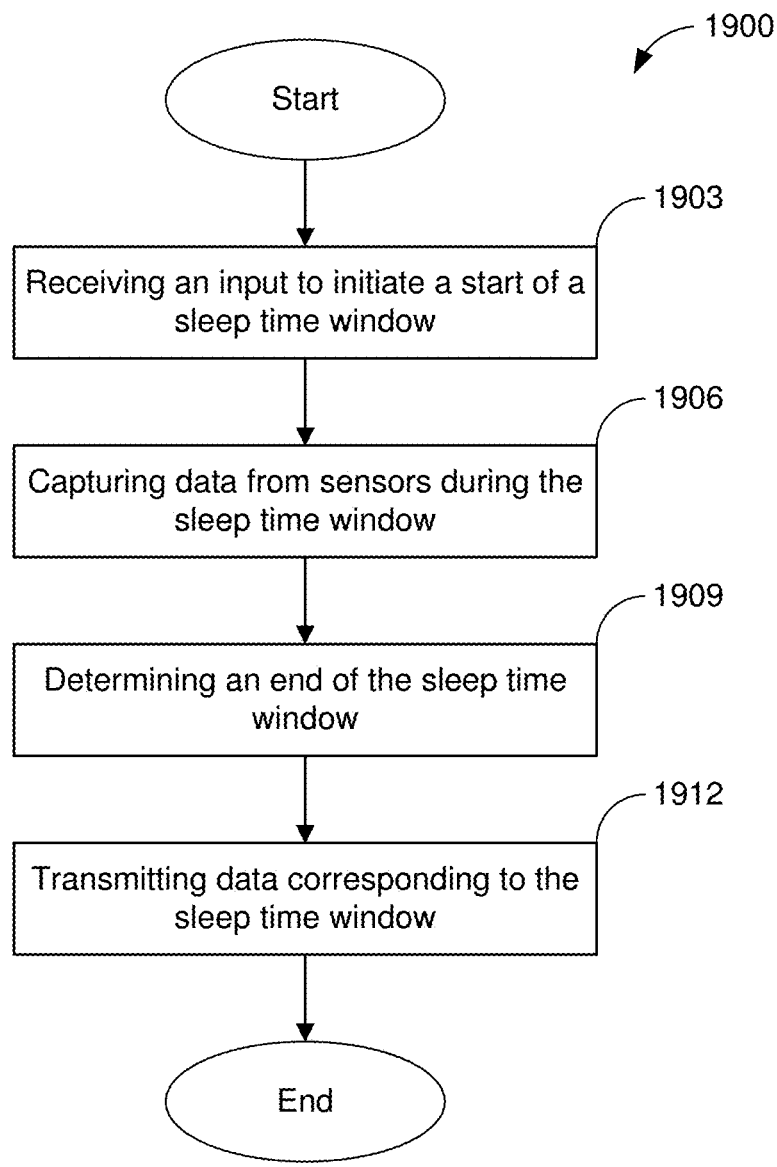

With reference to FIG. 19, shown is a flow chart of a process 1900 according to various embodiments of the present disclosure. In some embodiments, portions of the process 1900 can be performed via a patch device 103 (FIG. 1).

At box 1903, the process 1900 includes receiving an input to initiate a start of a sleep time window. For example, the patch application 218 can receive an input to initiate a start of a sleep time window. The patch application 218 can receive an input from a button push of an input device (e.g., a physical button, a touch screen, a USB input device such as a keyboard, mouse, or button push device) to initiate a sleep time window or collecting of data. In some embodiments, the patch application 218 can be configured to start and stop the sleep time window at a predetermined time, such as at 9:00 PM and 7:00 AM. In some embodiments, the testing service 233 can send a start command to the patch application 218 via the network, and the patch application 218 can initiate the start of the sleep time window (e.g., the testing time window/period) once the command is received. In one embodiment, the patch application 218 can monitor sensor measurements from sensors 221. When the sensor measurements exceed a configurable accuracy threshold, the patch application 218 can start collection of data (e.g., the sleep time window). As an example, the patch application 218 can determine that 95% of heart beats or more of a heart beat signal can be successfully detected. The patch application 218 may determine by analyzing a signal that a value jumps around quickly indicating that incomplete data or corrupt is being received. Once the values consistently stay within a predetermined range with a rate of change of the measurements being within another predetermined range, the patch application 218 can initiate the sleep time window.

At box 1906, the process 1900 includes capturing data from sensors during the sleep time window. For example, the patch application 218 can read sensor measurements from various sensors 221. The patch application 218 can store the sensor measurements in the data store 215. The patch application 218 can read from a clock and associate each sensor measurement with a time (e.g., timestamp) when the measurement occurred or was stored. In some embodiments, the patch application 218 can aggregate sensor measurements together and associate the collection with a time when stored in sensor data 224. As an example, the patch application 218 can determine two or more health parameters (e.g., SpO2 value, a heart rate, an RIAV, an RIIV, a RIFV, a respiratory rate) and store these parameters together with a single time value.

The patch application 218 can capture and aggregate the collection of sensor measurements on a predetermined frequency (e.g. 100 times per second, 60 times per second, 30 times per second, 10 times per second, 1 time per second, etc.). The patch application 218 can store rolling historical data in memory and compute additional statistics. As an example, the patch application 218 can store the health parameters in one buffer every 1 second for two minutes, in another buffer every 10 seconds for 10 minutes, in another buffer every 1 minute for 60 minutes, and in another buffer every hour for 24 hours. The patch application 218 can write these values to the data store 215 for later processing. The patch application 218 can compute an average for each health parameter from the buffers and store those averages in the data store 215 (e.g., average health parameters over two minutes, over ten minutes, over one hour, and over twenty four hours). The patch application 218 can store the averages on a predetermined frequency.

At box 1909, the process 1900 includes determining an end of the sleep time window. For example, the patch application 218 can determine an end of the sleep window. Similar to the start of the sleep time window, the patch application 218 can receive an input, a command, or trigger a stoppage of the sleep time window when preconfigured criteria are met (e.g., a time threshold has been met, specific measurement results have been achieved, a signal quality has falling below a predetermined threshold, etc.). In one embodiment, the patch application 218 can stop the sleep time window and automatically start a new sleep time window. For example, the patch application 218 can be configured to stop at noon each day and start a new time window at the same time to capture 24 hour testing windows.

At box 1912, the process 1900 includes transmitting data corresponding to the sleep time window. For example, the patch application 218 can transmit data corresponding to the sleep time window to the testing service 233 for storage in the test data 245 associated with a user account. The patch application 218 can package the sensor data 224 and result data 227 into a conveniently transferrable or predetermined format or coding scheme (e.g., XML, JSON, etc.). The patch application 218 can transmit the data over the network 206, which may be encrypted to protect the integrity of the patient's data. In some embodiments, the patch application 218 can receive confirmation of transfer from the testing service 233. In one embodiment, the patch application 218 can wipe the data from the data store 215 once the confirmation of transfer is received.

Figure 20:
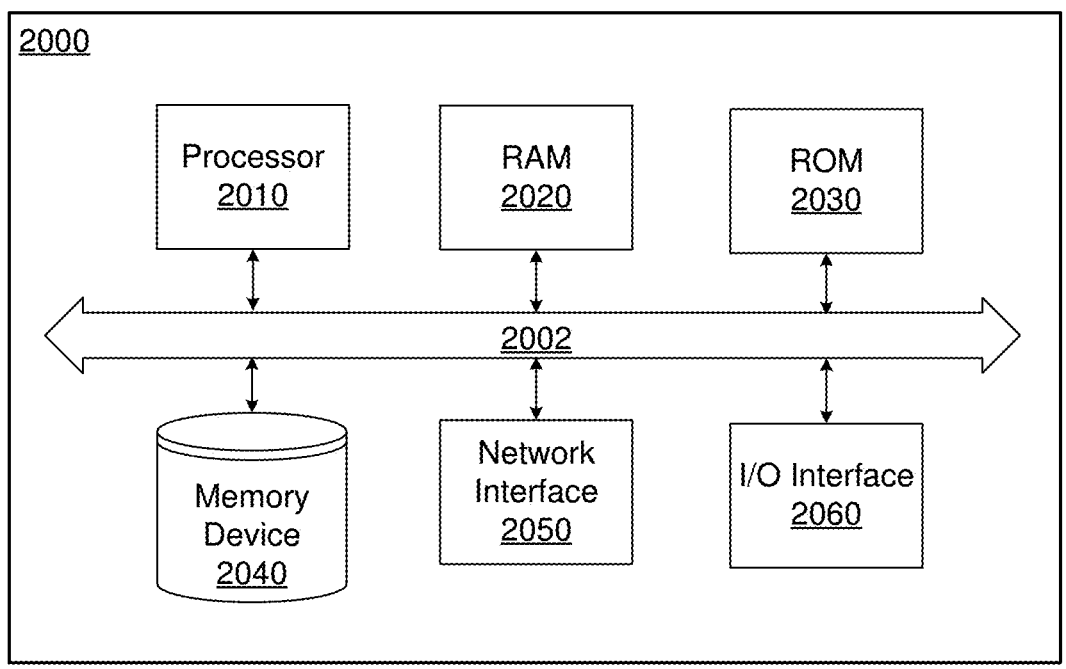
FIG. 20 is a schematic block diagram that provides one example illustration of a computing device of a patch device or computing environment employed in the sensing environment of FIG. 2 according to various embodiments of the present disclosure.

With reference to FIG. 20, shown is a schematic block diagram of the computing device 2000 according to an embodiment of the present disclosure. The patch device 103 (FIG. 1) and computing environment 203 (FIG. 2) can include one or more computing devices 2000. Each computing device 2000 includes at least one processor circuit, for example, having a processor 2010 and a memory 2040, both of which are coupled to a local interface 2002. The computing device 2000 can include a RAM 2020, a ROM 2030, a network interface 2050, and an I/O interface 2060. To this end, each computing device 2000 may include, for example, an embedded microprocessor, at least one server computer, or like device. The local interface 2002 may include, for example, a data bus with an accompanying address/control bus or other bus structure as can be appreciated.

Stored in the memory 2040 are both data and several components that are executable by the processor 2010. In particular, stored in the memory 2040 and executable by the processor 2010 are patch application 218 and testing service 233, and potentially other applications. Also stored in the memory 2040 may be a data store 215, data store 236, and other data. In addition, an operating system may be stored in the RAM 2020, ROM 2030, and/or memory 2040 and executable by the processor 2010.

It is understood that there may be other applications that are stored in the memory 2040 and are executable by the processor 2010 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, or other programming languages.

A number of software components are stored in the memory 2040 and are executable by the processor 2010. In this respect, the term "executable" means a program file that is in a form that can ultimately be run by the processor 2010. Examples of executable programs may be, for example, a compiled program that can be translated into machine code in a format that can be loaded into a random access portion of the memory 2040 and run by the processor 2010, source code that may be expressed in proper format such as object code that is capable of being loaded into a random access portion of the memory 2040 and executed by the processor 2010, or source code that may be interpreted by another executable program to generate instructions in a random access portion of the memory 2040 to be executed by the processor 2010, etc. An executable program may be stored in any portion or component of the memory 2040 including, for example, random access memory (RAM) 2020, read-only memory (ROM) 2030, hard drive, solid-state drive, USB flash drive, memory card, optical disc such as compact disc (CD) or digital versatile disc (DVD), floppy disk, magnetic tape, or other memory components.

The memory 2040 is defined herein as including both volatile and nonvolatile memory and data storage components. Volatile components are those that do not retain data values upon loss of power. Nonvolatile components are those that retain data upon a loss of power. Thus, the memory 2040 may include, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may include, for example, static random access memory (SRAM), dynamic random access memory (DRAM), or magnetic random access memory (MRAM) and other such devices. The ROM may include, for example, a programmable read-only memory (PROM), an erasable programmable read-only memory (EPROM), an electrically erasable programmable read-only memory (EEPROM), or other like memory device.

Also, the processor 2010 may represent multiple processors 2010 and/or multiple processor cores and the memory 2040 may represent multiple memories 2040 that operate in parallel processing circuits, respectively. In such a case, the local interface 2002 may be an appropriate network that facilitates communication between any two of the multiple processors 2010, between any processor 2010 and any of the memories 2040, or between any two of the memories 2040, etc. The local interface 2002 may include additional systems designed to coordinate this communication, including, for example, performing load balancing. The processor 2010 may be of electrical or of some other available construction.

Although the patch application 218 and testing service 233 and other various systems described herein may be embodied in software or code executed by processor hardware as discussed above, as an alternative the same may also be embodied in dedicated hardware or a combination of software and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc.

The flowcharts of FIGS. 18 and 19 show the functionality and operation of an implementation of portions of the patch application 218 and testing service 233. If embodied in software, each block may represent a module, segment, or portion of code that includes program instructions to implement the specified logical function(s). The program instructions may be embodied in the form of source code that includes human-readable statements written in a programming language or machine code that includes numerical instructions recognizable by a suitable execution system such as a processor 2010 in a computer system or other system. The machine code may be converted from the source code, etc. If embodied in hardware, each block may represent a circuit or a number of interconnected circuits to implement the specified logical function(s).

Although the flowcharts of FIGS. 18 and 19 show a specific order of execution, it is understood that the order of execution may differ from that which is depicted. For example, the order of execution of two or more blocks may be scrambled relative to the order shown. Also, two or more blocks shown in succession in FIGS. 18 and 19 may be executed concurrently or with partial concurrence. Further, in some embodiments, one or more of the blocks shown in FIGS. 18 and 19 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the patch application 218 and testing service 233, that includes software or code can be embodied in any non-transitory computer-readable medium for use by or in connection with an instruction execution system such as, for example, a processor 2010 in a computer system or other system. In this sense, the logic may include, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can include any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) 2020 including, for example, static random access memory (SRAM) and dynamic random access memory (DRAM), or magnetic random access memory (MRAM). In addition, the computer-readable medium may be a read-only memory (ROM) 2030, a programmable read-only memory (PROM), an erasable programmable read-only memory (EPROM), an electrically erasable programmable read-only memory (EEPROM), or other type of memory device.

Further, any logic or application described herein, including the patch application 218 and testing service 233, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device 2000, or in multiple computing devices in the same computing environment 203. Additionally, it is understood that terms such as "application," "service," "system," "engine," "module," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications May be made to the above-described embodiment(s) without departing substantially from the spirit and principles of the disclosure. All such modifications and variations are intended to be included herein within the scope of this disclosure and protected by the following claims.

What is claimed is:

1. A patch device comprising:
   a photoplethysmography (PPG) sensor comprising at least one light emitting diode (LED);
   a seismocardiography (SCG) sensor comprising a three-axis sensor;
   an adhesive layer configured to adhere to skin of a chest of an individual;
   one or more rigid components connected to the adhesive layer, the one or more rigid components comprising a hardware processor for communication with the PPG sensor and the SCG sensor, the hardware processor configured to receive a plurality of measurements from each of the PPG sensor and the SCG sensor; and
   an air gap between a lower surface of the adhesive layer and a lower surface of the PPG sensor for providing a compressive downward force when the adhesive layer and the PPG sensor are in contact with the skin of the chest of the individual, thereby improving signal quality of the PPG sensor, wherein:
   the PPG sensor passes through the adhesive layer;
   the adhesive layer and the PPG sensor are configured to be in contact with the skin of the chest of the individual simultaneously with at least a portion of the air gap therebetween.

2. The patch device of claim 1, further comprising a plurality of sensors comprising a gyroscope, an accelerometer, a compass, wherein the hardware processor is configured to determine a plurality of cardiorespiratory parameters via chest accelerometry based on the plurality of sensors.

3. The patch device of claim 2, wherein:
   the hardware processor is further configured to determine inertial measures of thoracoabdominal movement; and
   the plurality of cardiorespiratory parameters are determined based at least in part on the inertial measures of thoracoabdominal movement.

4. The patch device of claim 3, wherein the hardware processor is further configured to:
   measure, via the PPG sensor, cutaneous blood flow and volume; and
   determine blood oxygen saturation (SpO2) derived from the cutaneous blood flow and volume.

5. The patch device of claim 4, further comprising an electrocardiogram (ECG) sensor, wherein the hardware processor is further configured to determine heart rate variability based on measurements from the PPG sensor, the SCG sensor, and the ECG sensor.

6. The patch device of claim 1, further comprising a plurality of flexible layers.

7. The patch device of claim 6, wherein the plurality of flexible layers comprise:
   a silver layer;
   a dielectric layer; and
   a printed circuit board layer.

8. The patch device of claim 1, wherein the PPG sensor further comprises an array board comprising the at least one LED.

9. The patch device of claim 8, wherein the PPG sensor further comprises an adaptive filter configured to reduce a noise of readings from the array board.

10. The patch device of claim 1, wherein the SCG sensor further comprises a first analog to digital converter.

11. The patch device of claim 1, wherein the PPG sensor is configured to be positioned over and in contact with the chest of the individual via the adhesive layer.

12. The patch device of claim 1, wherein the air gap is less than or equal to 5.25 mm.

13. The patch device of claim 1, further comprising a digital signal processor circuit and a second analog to digital converter.

14. The patch device of claim 1, wherein the plurality of measurements describe at least one analog waveform.

15. The patch device of claim 1, wherein the hardware processor is further configured to:
   identify an amplitude of a signal from the PPG sensor;
   determine that the amplitude of the signal exceeds a predetermined threshold; and
   in response to the amplitude exceeding the predetermined threshold, generate an indication that the patch device is improperly applied to the chest of the individual.

16. The patch device of claim 15, wherein the amplitude corresponds to at least one of a red signal or an infrared signal.

17. The patch device of claim 1, wherein the patch device comprises a rectangular prism shape with a size of between 11 and 16 millimeters deep by between 42 and 47 millimeters long by between 32 and 37 millimeters wide.

18. The patch device of claim 1, wherein the air gap is at least 0.1 mm.

19. The patch device of claim 1, wherein the one or more rigid components are connected to a first side of the adhesive layer.

20. The patch device of claim 1, wherein the PPG sensor comprises a plurality of LEDs.

* * * * *